United States Patent
Agami et al.

(10) Patent No.: US 12,383,442 B2
(45) Date of Patent: *Aug. 12, 2025

(54) PACKAGED FEMININE HYGIENE PAD PRODUCT ADAPTED FOR DISCREET CARRY AND ACCESS, AND MANUFACTURING PROCESS

(71) Applicant: The Procter & Gamble Company, Cincinnati, OH (US)

(72) Inventors: Sion Agami, Cincinnati, OH (US); Dale F. Bittner, Hamilton, OH (US); Ryan Leroy Breehne, Cincinnati, OH (US); Angila Ann Darcy, Cincinnati, OH (US); Benjamin Philip Goodman, Cincinnati, OH (US); Mathias J. Hilpert, Mason, OH (US); Andrew Saksa, Cincinnati, OH (US); Curtis H. Van Valkenburgh, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/731,831

(22) Filed: Jun. 3, 2024

(65) Prior Publication Data

US 2024/0315891 A1    Sep. 26, 2024

Related U.S. Application Data

(63) Continuation of application No. 16/750,082, filed on Jan. 23, 2020, now Pat. No. 12,036,105.
(Continued)

(51) Int. Cl.
*A61F 13/551* (2006.01)
*A61F 13/15* (2006.01)
(Continued)

(52) U.S. Cl.
CPC .... *A61F 13/5514* (2013.01); *A61F 13/15682* (2013.01); *A61F 13/15747* (2013.01);
(Continued)

(58) Field of Classification Search
CPC .... A61F 13/511; A61F 13/512; A61F 13/514; A61F 13/551; A61F 13/53; A61F 13/58;
(Continued)

(56) References Cited

U.S. PATENT DOCUMENTS

| | | | |
|---|---|---|---|
| 3,619,336 A | 11/1971 | Hughes | |
| 4,405,310 A | 9/1983 | Karami | |

(Continued)

FOREIGN PATENT DOCUMENTS

| | | |
|---|---|---|
| CA | 2785189 A1 | 7/2011 |
| CN | 1074110 A | 7/1993 |

(Continued)

OTHER PUBLICATIONS

All Office Actions; U.S. Appl. No. 18/743,212, filed Jun. 14, 2024.
(Continued)

*Primary Examiner* — Michele Kidwell
(74) *Attorney, Agent, or Firm* — Sarah M. DeCristofaro

(57) ABSTRACT

A product including a feminine hygiene pad provided in a folded configuration within an individualized package is disclosed. The pad is folded separately of the package and contained within the package. The pad may include a backsheet adhesive coversheet including a section of polymeric film adhered to an outward-facing side of the backsheet of the pad, and a deposit of backsheet adhesive disposed between the backsheet adhesive coversheet and the backsheet, the backsheet adhesive coversheet and the backsheet adhesive being selected and adapted such that the backsheet adhesive coversheet may be peeled away from the pad to expose the backsheet adhesive without substantial (Continued)

damage to a remainder of the pad, and such that the backsheet adhesive remains substantially in place and adhered to the backsheet following peeling away of the backsheet adhesive coversheet.

20 Claims, 14 Drawing Sheets

Related U.S. Application Data

(60) Provisional application No. 62/795,745, filed on Jan. 23, 2019.

(51) Int. Cl.
| | |
|---|---|
| *A61F 13/47* | (2006.01) |
| *A61F 13/511* | (2006.01) |
| *A61F 13/512* | (2006.01) |
| *A61F 13/514* | (2006.01) |
| *A61F 13/53* | (2006.01) |
| *A61F 13/531* | (2006.01) |
| *A61F 13/58* | (2006.01) |

(52) U.S. Cl.
CPC .... *A61F 13/15756* (2013.01); *A61F 13/4704* (2013.01); *A61F 13/512* (2013.01); *A61F 13/53* (2013.01); *A61F 13/531* (2013.01); *A61F 2013/1591* (2013.01); *A61F 2013/51147* (2013.01); *A61F 2013/5147* (2013.01); *A61F 2013/530817* (2013.01); *A61F 2013/582* (2013.01)

(58) Field of Classification Search
CPC .............. A61F 2013/5147; A61F 13/15; A61F 13/47; A61F 13/531
See application file for complete search history.

(56) References Cited

U.S. PATENT DOCUMENTS

| | | | |
|---|---|---|---|
| 4,692,162 | A | 9/1987 | Binker et al. |
| 5,242,726 | A | 9/1993 | Pariseau |
| 5,295,988 | A | 3/1994 | Muckenfuhs et al. |
| 5,358,499 | A | 10/1994 | Seidy |
| 5,873,869 | A | 2/1999 | Hammons et al. |
| 5,993,430 | A | 11/1999 | Gossens et al. |
| 6,293,932 | B1 | 9/2001 | Balzar et al. |
| 6,316,688 | B1 | 11/2001 | Hammons |
| 6,601,706 | B2 | 8/2003 | Mcmanus et al. |
| 7,334,682 | B2 | 2/2008 | Goepfert |
| 7,398,870 | B2 | 7/2008 | Mccabe |
| 9,186,284 | B1 | 11/2015 | Hernandez |
| 11,234,871 | B2 | 2/2022 | Kuramochi |
| 11,712,379 | B2 | 8/2023 | Agami et al. |
| 12,036,105 | B2 * | 7/2024 | Agami ............... A61F 13/472 |
| 2002/0084203 | A1 | 7/2002 | Cottingham et al. |
| 2002/0125105 | A1 | 9/2002 | Nakakado |
| 2002/0132106 | A1 | 9/2002 | Dyer et al. |
| 2003/0073962 | A1 | 4/2003 | Olsen et al. |
| 2004/0186450 | A1 | 9/2004 | Hermansson et al. |
| 2005/0131371 | A1 | 6/2005 | Fell |
| 2005/0137553 | A1 | 6/2005 | Bechyne et al. |
| 2005/0148979 | A1 | 7/2005 | Palma et al. |
| 2005/0154365 | A1 | 7/2005 | Zander et al. |
| 2005/0261651 | A1 | 11/2005 | Lima et al. |
| 2006/0025739 | A1 | 2/2006 | Dipalma |
| 2007/0233031 | A1 | 10/2007 | Benson |
| 2009/0105680 | A1 | 4/2009 | Amiot et al. |
| 2009/0105681 | A1 | 4/2009 | Chicoine et al. |
| 2010/0262090 | A1 | 10/2010 | Riesinger |
| 2011/0028931 | A1 | 2/2011 | Fung |
| 2013/0190711 | A1 | 7/2013 | Hashino et al. |
| 2015/0119837 | A1 | 4/2015 | Thompson, Jr. et al. |
| 2015/0313763 | A1 | 11/2015 | Bagger-sjbck |
| 2015/0374560 | A1 | 12/2015 | Hubbard, Jr. |
| 2016/0089279 | A1 | 3/2016 | Barbosa et al. |
| 2016/0235592 | A1 | 8/2016 | Coe et al. |
| 2016/0287452 | A1 | 10/2016 | Hubbard, Jr. |
| 2017/0112678 | A1 | 4/2017 | Pelland |
| 2017/0151105 | A1 | 6/2017 | Holmberg |
| 2018/0353354 | A1 | 12/2018 | Lee et al. |
| 2019/0254890 | A1 | 8/2019 | Yonaha |
| 2020/0229985 | A1 | 7/2020 | Agami et al. |
| 2020/0229990 | A1 | 7/2020 | Agami et al. |
| 2020/0229991 | A1 | 7/2020 | Agami et al. |
| 2023/0310231 | A1 | 10/2023 | Agami et al. |

FOREIGN PATENT DOCUMENTS

| | | |
|---|---|---|
| CN | 1087511 A | 6/1994 |
| CN | 1163096 A | 10/1997 |
| CN | 1168292 A | 12/1997 |
| CN | 1177359 A | 3/1998 |
| CN | 1368870 A | 9/2002 |
| CN | 1439348 A | 9/2003 |
| CN | 1625377 A | 6/2005 |
| CN | 1875900 A | 12/2006 |
| CN | 101600407 A | 12/2009 |
| CN | 102470053 A | 5/2012 |
| CN | 102665629 A | 9/2012 |
| CN | 102753126 A | 10/2012 |
| CN | 103356343 A | 10/2013 |
| CN | 104640576 A | 5/2015 |
| CN | 104869965 A | 8/2015 |
| CN | 106456412 A | 2/2017 |
| CN | 107249537 A | 10/2017 |
| CN | 107530211 A | 1/2018 |
| CN | 108135762 A | 6/2018 |
| CN | 108882995 A | 11/2018 |
| GB | 2277914 B | 6/1997 |
| JP | 2004298288 A | 10/2004 |
| JP | 2005176869 A | 7/2005 |
| JP | 2018535743 A | 12/2018 |
| WO | 9414396 A1 | 7/1994 |
| WO | 03039424 A1 | 5/2003 |
| WO | 2004069684 A1 | 8/2004 |
| WO | 2007041212 A1 | 4/2007 |
| WO | 2007086034 A1 | 8/2007 |
| WO | 2009136826 A1 | 11/2009 |
| WO | 2013080757 A1 | 6/2013 |

OTHER PUBLICATIONS

All Office Actions; U.S. Appl. No. 18/743,219, filed Jun. 14, 2024.
U.S. Appl. No. 18/743,212, filed Jun. 14, 2024, to Chad Burnett et al.
U.S. Appl. No. 18/743,219, filed Jun. 14, 2024, to Chad Burnett et al.
All Office Actions: U.S. Appl. No. 18/329,848, filed Jun. 6, 2023.
All Office Actions; U.S. Appl. No. 16/750,074 filed Jan. 23, 2020.
All Office Actions; U.S. Appl. No. 16/750,082, filed Jan. 23, 2020.
All Office Actions; U.S. Appl. No. 16/750,089, filed Jan. 23, 2020.
All Office Actions; U.S. Appl. No. 16/750,095, filed Jan. 23, 2020.
PCT Search Report and Written Opinion for PCT/US2020/014751 dated May 4, 2020, 14 pages.
PCT Search Report and Written Opinion for PCT/US2020/014755 dated Mar. 26, 2020, 13 pages.
PCT Search Report and Written Opinion for PCT/US2020/014756 dated Mar. 30, 2020, 14 pages.
PCT Search Report and Written Opinion for PCT/US2020/014764 dated May 4, 2020, 11 pages.

* cited by examiner

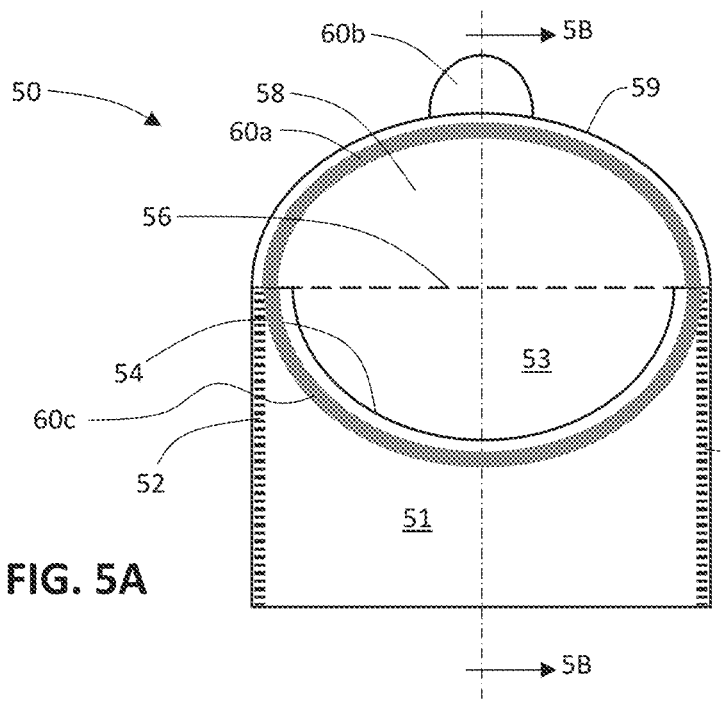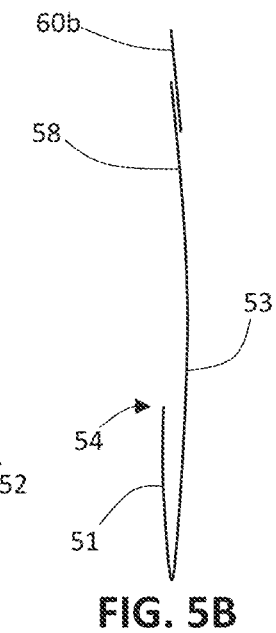
FIG. 5A
FIG. 5B
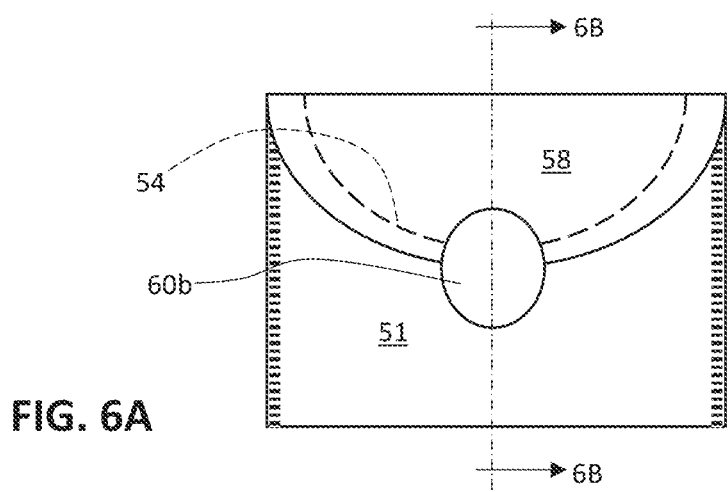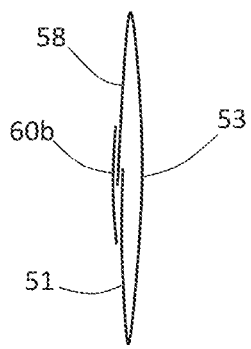
FIG. 6A
FIG. 6B

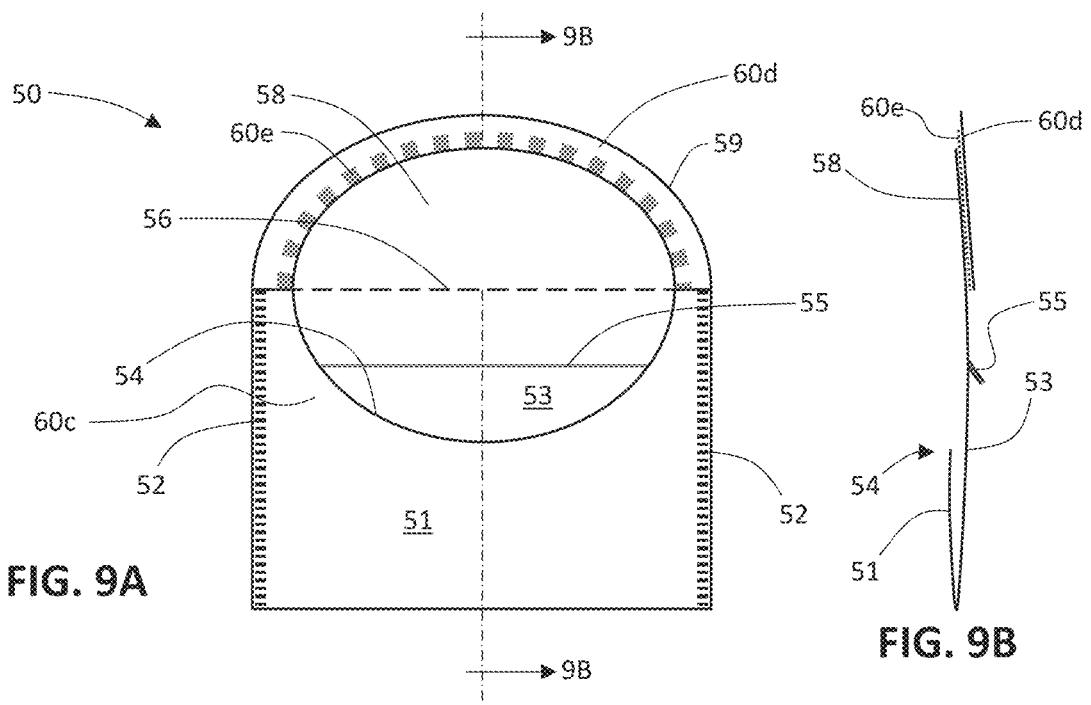
FIG. 9A
FIG. 9B
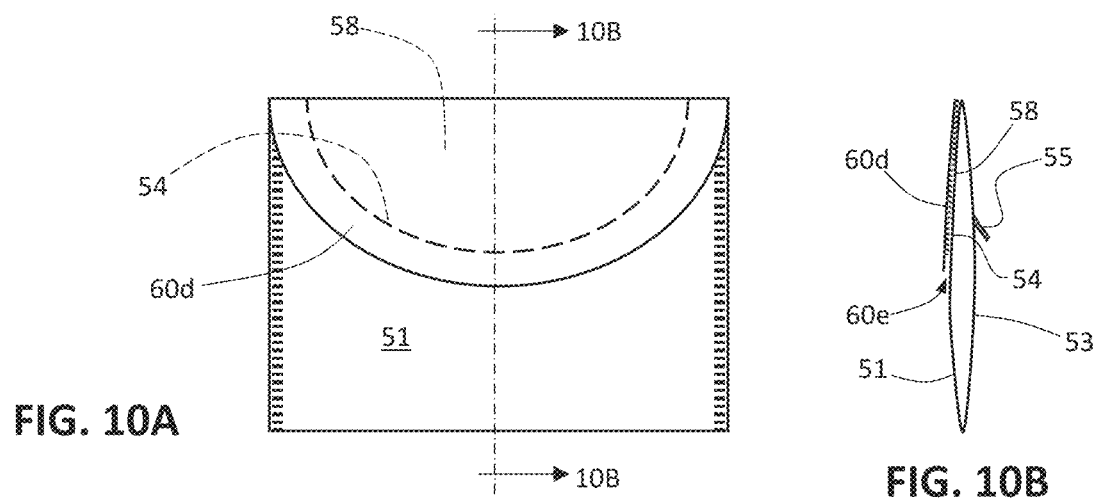
FIG. 10A
FIG. 10B

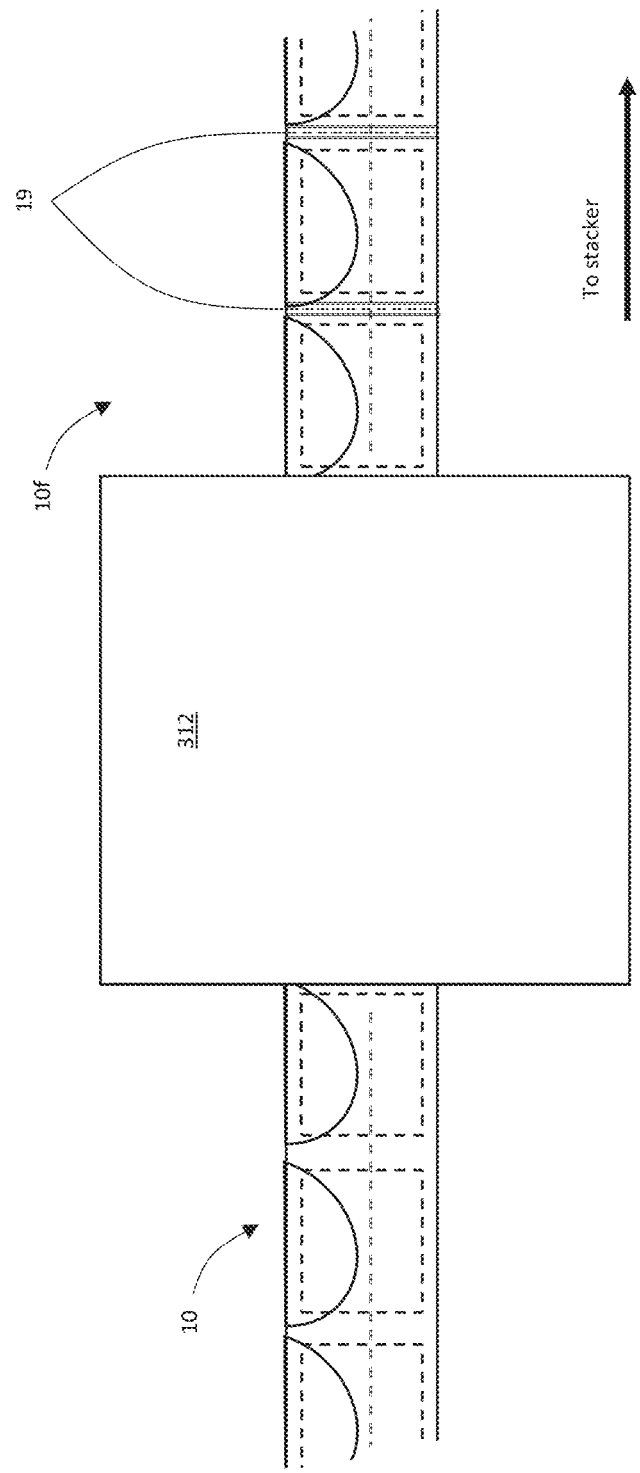

PACKAGED FEMININE HYGIENE PAD PRODUCT ADAPTED FOR DISCREET CARRY AND ACCESS, AND MANUFACTURING PROCESS

CROSS REFERENCE TO RELATED APPLICATION

This application is a continuation of, and claims priority under 35 U.S.C. § 120 to, U.S. patent application Ser. No. 16/750,082 filed on Jan. 23, 2020, which claims the benefit, under 35 U.S.C. § 119(c), of U.S. Provisional Patent Application Ser. No. 62/795,745, filed Jan. 23, 2019, the entire disclosures of all of which are fully incorporated by reference herein.

BACKGROUND

Users/consumers of feminine hygiene pads have developed a number of varying expectations and preferences for such products over the years, as the products themselves have evolved. These expectations and preferences include (in no particular order) (1) that the pad have suitable absorption performance such that it will readily accept, absorb, contain, isolate and effectively retain all menstrual fluid discharged, away from the user's skin and without leaking, over a normal time of use/wear; (2) that the pad be as thin (non-bulky), flexible and pliable as possible for purposes of comfort, accommodation of the wearer's body movements, and discreetness of wear under clothing; and (3) that the pad and its packaging provide for convenient and discreet carry, and discreet and easy package opening and access to the pad at the time it is needed (particularly when the user is away from home). Many women may have anxiety about leaving the home during menstruation, and about being sufficiently prepared, while away from home, to effectively address needs relating to absorption and containment of discharged menstrual fluid. In addition to desiring a sufficiently absorbent pad that can be effectively used/worn discreetly under clothing, many women desire discreetness and convenience with respect to having to carry pads with them outside the home, and with respect to having to open and access a packaged pad for use, in situations in which they need to use a bathroom or restroom in an unfamiliar, non-private or otherwise uncomfortable place and/or circumstances.

With respect to currently known product designs and the materials currently known and used as components of these products, these expectations and preferences cannot all be fully satisfied simultaneously. The manufacturer must carefully balance its priorities, to provide product features that address each of these expectations and preferences to greater and lesser extents under competitive cost/pricing constraints, in order to provide a product that will sufficiently please its user/consumer market. For example, absorbent materials that desirably provide absorption capacity also undesirably contribute to bulk when packaged and when worn under clothing, and may also limit flexibility of the pad. Accordingly, when designing its products for maximized consumer satisfaction, the manufacturer must make choices concerning how to prioritize design features and materials selections that affect these characteristics, to strike a balance that will hopefully maximize satisfaction of its consumer market.

Consequently, there is always room for any improvements that can more satisfactorily and simultaneously address consumer preferences for convenience and discreetness of package carry, opening and access, combined with absorption performance.

DESCRIPTION OF THE FIGURES

FIG. 5A is a front view of an envelope package in an opened configuration.

FIG. 5B is a schematic cross section of the package as shown in FIG. 5A, taken along line 5B-5B in FIG. 5A.

FIG. 6A is a front view of an envelope package in a closed configuration.

FIG. 6B is a schematic cross section of the package as shown in FIG. 6A, taken along line 6B-6B in FIG. 6A.

FIG. 9A is a front view of another example of an envelope package in an opened configuration.

FIG. 9B is a schematic cross section of the package as shown in FIG. 9A, taken along line 9B-9B in FIG. 9A.

FIG. 10A is a front view of an another example of an envelope package in a closed configuration.

FIG. 10B is a schematic cross section of the package as shown in FIG. 10A, taken along line 10B-10B in FIG. 10A.

FIG. 11B is a schematic plan view depiction of an alternative example of a portion of the process flow depicted in FIG. 11A.

DESCRIPTION OF EXAMPLES

Definitions

With respect to a feminine hygiene pad that is open and laid out flat on a horizontal planar surface, "lateral" refers to a direction perpendicular to the longitudinal direction and parallel the horizontal planar surface. "Width" refers to a dimension measured along a lateral direction.

With respect to a feminine hygiene pad that is open and laid out flat on a horizontal planar surface and having a length measured from its forwardmost end to its rearwardmost end, "longitudinal" refers to a direction parallel with the line along which the length is measured, and parallel to the horizontal planar surface. "Length" refers to a dimension measured in the longitudinal direction.

With respect to a feminine hygiene pad, the terms "front," "rear," "forward" and "rearward" relate to features or regions of the pad in a position as it would ordinarily be worn by a user, and the front and rear of the user's body when standing.

With respect to a feminine hygiene pad that is open and laid out flat on a horizontal planar surface, "z-direction" refers to a direction perpendicular to the horizontal planar surface. When the pad is being worn by a user (and thus in a curved configuration), "z-direction" at any particular point location on the pad refers to a direction normal to the wearer-facing surface of the pad at the particular point location.

With respect to a feminine hygiene pad, "wearer-facing" is a relative locational term referring to a feature of a component or structure of the pad that when in use that lies closer to the wearer than another feature of the component or structure that lies along the same z-direction. For example, a topsheet has a wearer-facing surface that lies closer to the wearer than the opposite, outward-facing surface of the topsheet.

With respect to a feminine hygiene pad, "outward-facing" is a relative locational term referring to a feature of a component or structure of the pad that when in use that lies farther from the wearer than another feature of the component or structure that lies along the same z-direction. For example, a topsheet has an outward-facing surface that lies farther from the wearer than the opposite, wearer-facing surface of the topsheet.

Description

Figure 1:
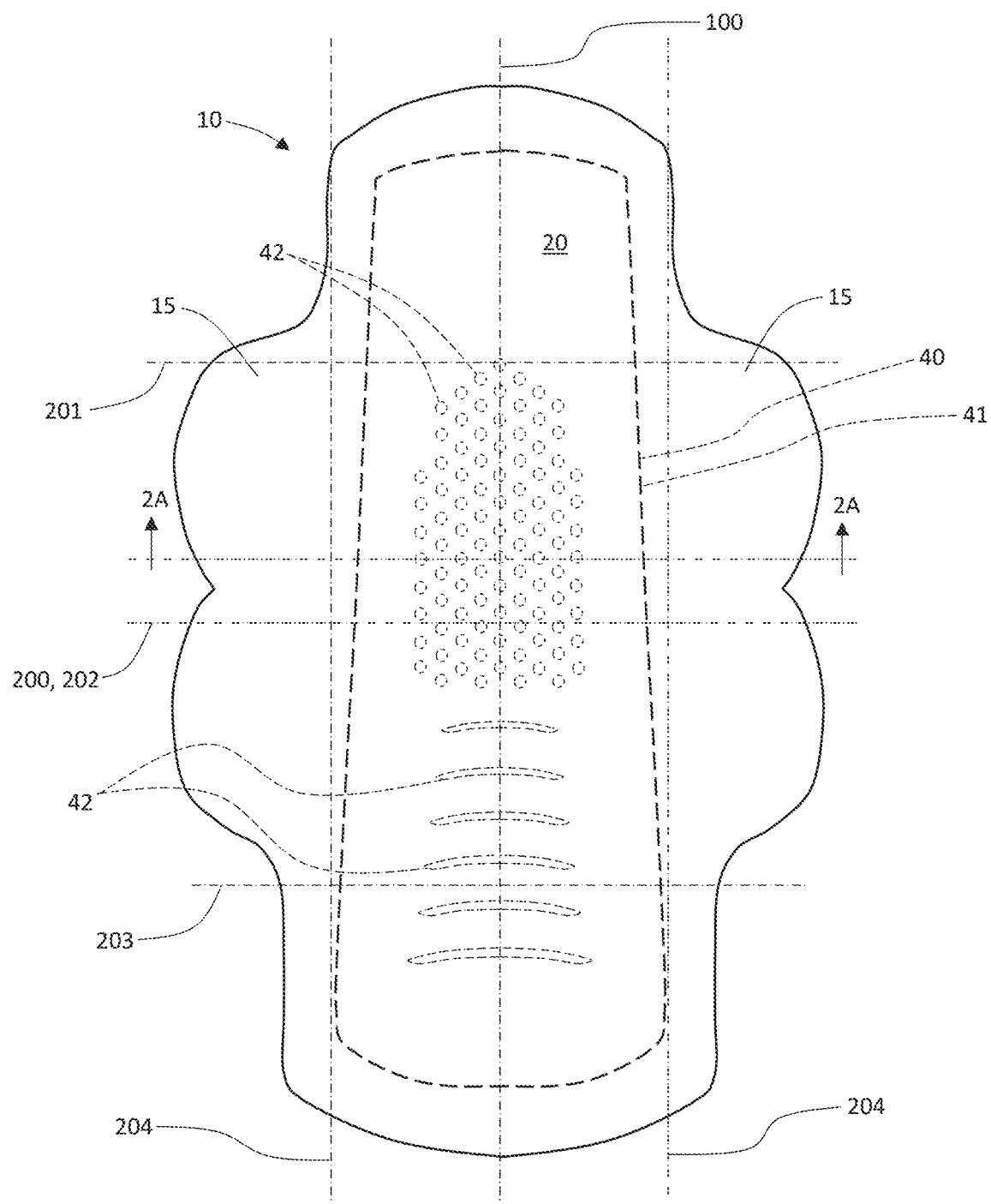
FIG. 1 is a plan view of a feminine hygiene pad, open and laid out flat, topsheet side facing the viewer.
Figure 2A:
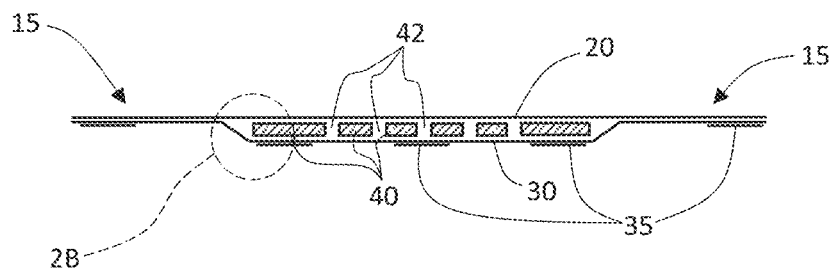
FIG. 2A is a schematic lateral cross section of the feminine hygiene pad of FIG. 1, taken along line 2A-2A in FIG. 1.

Referring to FIGS. 1 and 2A, a feminine hygiene pad 10 may include a liquid permeable topsheet 20, a liquid impermeable backsheet 30 and an absorbent layer 40 disposed between the topsheet and the backsheet. The absorbent layer has an outer perimeter 41. In peripheral regions outside the outer perimeter 41, the topsheet and the backsheet may be bonded together in laminated fashion by any suitable mechanism including but not limited to adhesive bonding, thermal bonding, pressure bonding, etc., thereby retaining and holding the absorbent layer 40 in place between the topsheet 20 and the backsheet 30. Pad 10 may include opposing wing portions 15 extending laterally outside of perimeter 41 by a comparatively greater width dimension than the main portion of the pad. Wing portions 15 may be formed of lateral extensions of the material forming the topsheet 20, backsheet 30, or both together. The outward-facing surface of the backsheet forming the undersides of the main portion and the wing portions may have deposits of adhesive 35 thereon. Adhesive deposits 35 may be provided to enable the user to adhere the pad to the inside of her underpants in the crotch region thereof, and wrap the wing portions through and around the inside edges of the leg openings of the underpants and adhere them to the outside/underside of the underpants in the crotch region, providing supplemental holding support and helping guard the leg edges of the underpants against soiling. When pad 10 is packaged, adhesive deposits 35 may be covered by one or more removable sheets of release film or paper (not shown) that cover the adhesive deposits 35 and shield them from contact with other surfaces until the user is ready to remove the sheets and place the pad for use.

To ensure that the pad facilitates sufficiently compact folding and packaging as described herein, it may be desired to limit the length LP of the pad to no greater than 32 cm, more preferably no greater than 29 cm, and even more preferably no greater than 26 cm. Alternatively, or in addition, it may be desired to limit the length LAL of the absorbent layer (also measured in the longitudinal direction) to no greater than 30 cm, more preferably no greater than 27 cm, and even more preferably no greater than 24 cm.

Topsheet

Topsheet 20 may be formed of any suitable liquid permeable web material. Referring back to the figures, the topsheet 20 is positioned adjacent a wearer-facing surface of the absorbent layer 40 and may be joined thereto and to the backsheet 30 by any suitable attachment or bonding method. The topsheet 20 and the backsheet 30 may be joined directly to each other in the peripheral regions outside the perimeter 41 of the absorbent layer 40 and may be indirectly joined by directly joining them respectively to wearer-facing and outward-facing surfaces of the absorbent layer or additional optional layers included with the pad.

Topsheet 20 may be formed of any liquid pervious web material that is suitably compliant, soft feeling, and non-irritating to the wearer's skin. Suitable topsheet materials include a liquid pervious material that contacts the body of the wearer and permits menstrual fluid discharges to rapidly penetrate through it.

A suitable topsheet can be made of various materials such as woven and nonwoven materials; apertured film materials including apertured formed thermoplastic films, apertured plastic films, and fiber-entangled apertured films; hydroformed thermoplastic films; porous foams; reticulated foams; reticulated thermoplastic films; thermoplastic scrims; or combinations thereof. Some suitable examples of films that can be utilized as topsheets are described in U.S. Pat. Nos. 3,929,135; 4,324,246; 4,342,314; 4,463,045; 5,006,394; 4,609,518; and 4,629,643.

Nonlimiting examples of woven and nonwoven web materials that may be suitable for use as the topsheet include fibrous materials made from natural fibers, modified natural fibers, synthetic fibers, or combinations thereof. Some suitable examples are described in U.S. Pat. Nos. 4,950,264; 4,988,344; 4,988,345; 3,978,185; 7,785,690; 7,838,099; 5,792,404; and 5,665,452.

In some examples, the topsheet may comprise tufts as described in U.S. Pat. Nos. 8,728,049; 7,553,532; 7,172,801; 8,440,286; 7,648,752; and 7,410,683. The topsheet may have a pattern of discrete hair-like fibrils as described in U.S. Pat. No. 7,655,176 or U.S. Pat. No. 7,402,723. Additional examples of suitable topsheet materials include those described in U.S. Pat. Nos. 8,614,365; 8,704,036; 6,025,535 and US 2015/041640. Another suitable topsheet may be formed from a three-dimensional substrate as detailed in US 2017/0258647. The topsheet may have one or more layers, as described in US 2016/0167334; US 2016/0166443; and US 2017/0258651. The topsheet may be apertured, as described in U.S. Pat. No. 5,628,097.

As contemplated herein, component nonwoven web material from which topsheet 20 be cut may be a nonwoven web material that includes or consists predominately (by weight) or entirely of cellulosic plant fibers such as fibers of cotton, flax, hemp, jute or mixtures thereof, that are either naturally hydrophilic or suitably processed so as be rendered hydrophilic (or have increased hydrophilicity) and processed to be suitably soft. Plant-based fibers may be preferred to appeal to consumer preferences for natural products. In other examples, semisynthetic fibers derived from cellulosic material, such as rayon (including viscose, lyocell, MODAL (a product of Lenzing AG, Lenzing, Austria) and cuprammonium rayon) may be used. In some examples a topsheet cut from a carded nonwoven including or consisting predominately (by weight) or entirely of cotton fibers may be preferred. In some examples, the nonwoven web material may be formed via a carding process. In some other examples the nonwoven web material may be formed in a co-forming process in which plant-based fibers of finite lengths are physically blended or mixed with streams of filaments of indefinite lengths, spun from polymeric resin, and laid down on a forming belt to form a web as described in, for example, U.S. Pat. Nos. 8,017,534; 4,100,324; US 2003/0200991; U.S. Pat. No. 5,508,102; US 2003/0211802; EP 0 333 228; WO 2009/10938; US 2017/0000695; US 2017/0002486; U.S. Pat. No. 9,944,047; 2017/0022643 and US 2018/0002848.

For purposes of limiting bulk and caliper (thickness) of the pad for the purpose of providing a thin pad facilitating compact folding and packaging as described below, it may be desired that the topsheet be disposed in direct face-to-face relationship with the absorbent layer, with no intervening layer disposed therebetween. Alternatively, an intervening layer, if included (such as a secondary topsheet or acquisition layer), may be formed of a nonwoven web material having a basis weight no greater than 30 gsm, more preferably no greater than 25 gsm, even more preferably no greater than 20 gsm, and still more preferably no greater than 15 gsm.

Absorbent Layer

Figure 2B:
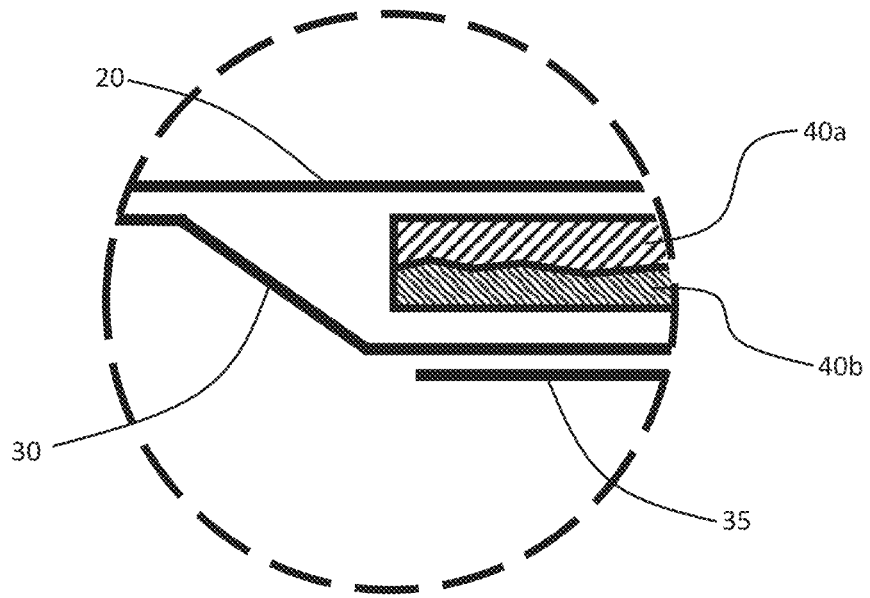
FIG. 2B is a view of portion 2B of the drawing of FIG. 2A, enlarged to depict sublayers of an absorbent layer.
Figure 3:
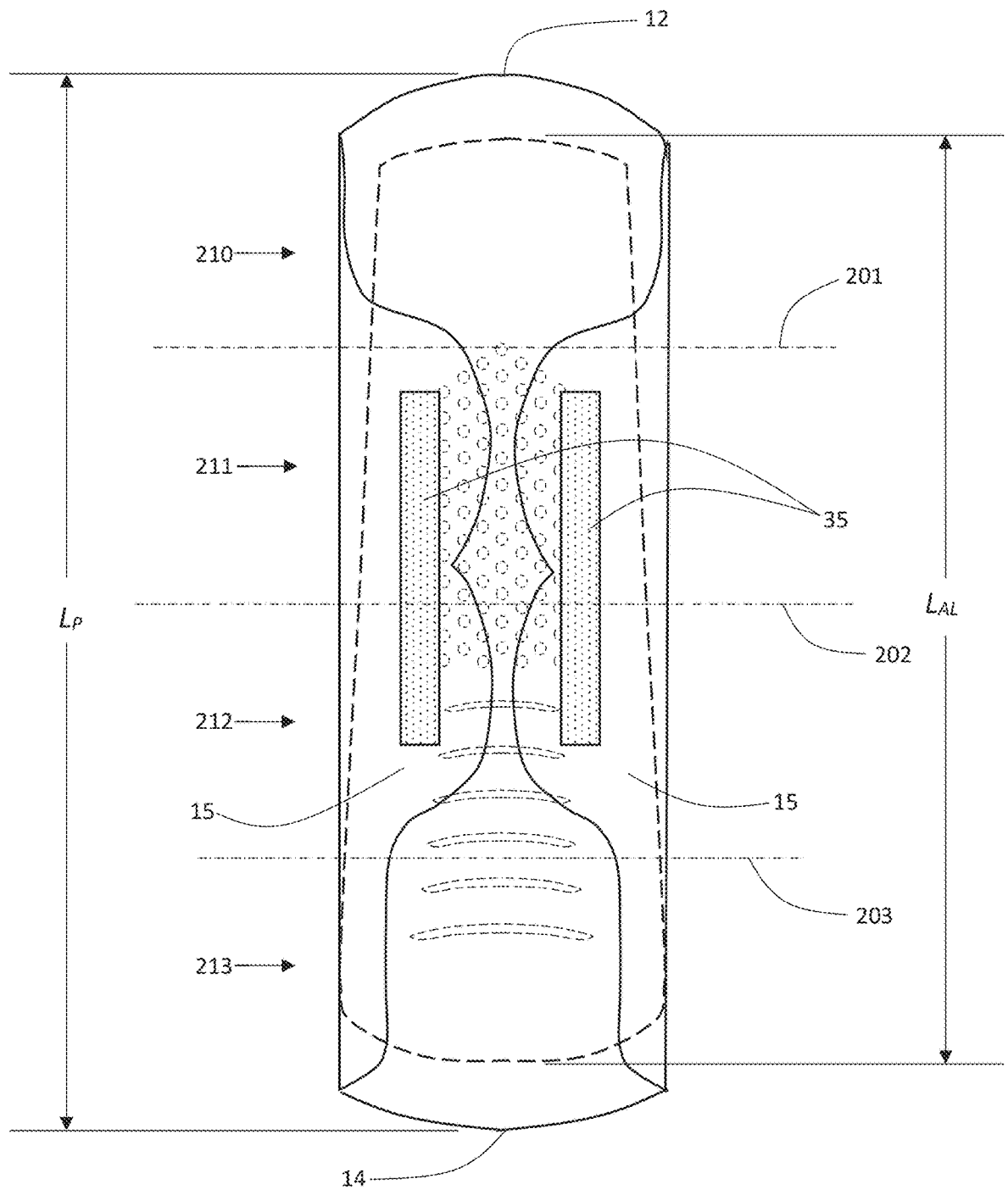
FIG. 3 is a plan view of the feminine hygiene pad of FIG. 1, shown with side portions folded laterally over and inwardly alongside longitudinal fold lines.

In some examples the absorbent layer 40 may be formed of or include a layer of absorbent open-celled foam material. In some examples, the foam material may include at least first and second sublayers 40a, 40b (FIG. 2B) of absorbent open-celled foam material, the sublayers being in direct face-to-face contact with each other. In such examples, the wearer-facing sublayer may be a relatively larger-celled foam material, and the outward-facing sublayer may be a relatively smaller-celled foam material, for purposes explained in more detail below. In some examples it may be desired that the layer of absorbent open-celled foam material provide the majority, substantially most or all of the absorption capacity of the pad. This feature minimizes the number of components present to impart bulk to the pad when folded and packaged, and when in use.

The open-celled foam material may be a foam material that is manufactured via polymerization of the continuous oil phase of a water-in-oil high internal phase emulsion ("HIPE").

A water-in-oil HIPE has two phases. One phase is a continuous oil phase comprising monomers to be polymerized, and an emulsifier to help stabilize the HIPE. The oil phase may also include one or more photoinitiators. The monomer component may be present in an amount of from about 80% to about 99%, and in certain examples from about 85% to about 95% by weight of the oil phase. The emulsifier component, which is soluble in the oil phase and suitable for forming a stable water-in-oil emulsion may be present in the oil phase in an amount of from about 1% to about 20% by weight of the oil phase. The emulsion may be formed at an emulsification temperature of from about 20° C. to about 130° C. and in certain examples from about 50° C. to about 100° C.

In general, the monomers will include from about 20% to about 97% by weight of the oil phase at least one substantially water-insoluble monofunctional alkyl acrylate or alkyl methacrylate. For example, monomers of this type may include C4-C18 alkyl acrylates and C2-C18 methacrylates, such as ethylhexyl acrylate, butyl acrylate, hexyl acrylate, octyl acrylate, nonyl acrylate, decyl acrylate, isodecyl acrylate, tetradecyl acrylate, benzyl acrylate, nonyl phenyl acrylate, hexyl methacrylate, 2-ethylhexyl methacrylate, octyl methacrylate, nonyl methacrylate, decyl methacrylate, isodecyl methacrylate, dodecyl methacrylate, tetradecyl methacrylate, and octadecyl methacrylate.

The oil phase may also comprise from about 2% to about 40%, and in certain examples from about 10% to about 30%, by weight of the oil phase, a substantially water-insoluble, polyfunctional crosslinking alkyl acrylate or methacrylate. This crosslinking comonomer, or crosslinker, is added to confer strength and resilience to the resulting HIPE foam. Examples of crosslinking monomers of this type comprise monomers containing two or more activated acrylate, methacrylate groups, or combinations thereof. Nonlimiting examples of this group include 1,6-hexanedioldiacrylate, 1,4-butanedioldimethacrylate, trimethylolpropane triacrylate, trimethylolpropane trimethacrylate, 1,1 2-dodecyldimethacrylate, 1,14-tetradecanedioldimethacrylate, ethylene glycol dimethacrylate, neopentyl glycol diacrylate (2,2-dimethylpropanediol diacrylate), hexanediol acrylate methacrylate, glucose pentaacrylate, sorbitan pentaacrylate, and the like. Other examples of crosslinkers contain a mixture of acrylate and methacrylate moieties, such as ethylene glycol acrylate-methacrylate and neopentyl glycol acrylate-methacrylate. The ratio of methacrylate:acrylate group in the mixed crosslinker may be varied from 50:50 to any other ratio as needed.

Any third substantially water-insoluble comonomer may be added to the oil phase in weight percentages of from about 0% to about 15% by weight of the oil phase, in certain examples from about 2% to about 8%, to modify properties of the HIPE foams. In certain cases, "toughening" monomers may be desired which impart toughness to the resulting HIPE foam. These include monomers such as styrene, vinyl chloride, vinylidene chloride, isoprene, and chloroprene. Without being bound by theory, it is believed that such monomers aid in stabilizing the HIPE during polymerization (also known as "curing") to provide a more homogeneous and better formed HIPE foam which results in better toughness, tensile strength, abrasion resistance, and the like. Monomers may also be added to confer flame retardancy as disclosed in U.S. Pat. No. 6,160,028. Monomers may be added to confer color, for example vinyl ferrocene, fluorescent properties, radiation resistance, opacity to radiation, for example lead tetraacrylate, to disperse charge, to reflect incident infrared light, to absorb radio waves, to form a wettable surface on the HIPE foam struts, or for any other desired property in a HIPE foam. In some cases, these additional monomers may slow the overall process of conversion of HIPE to HIPE foam, the tradeoff being necessary if the desired property is to be conferred. Thus, such monomers can be used to slow down the polymerization rate of a HIPE. Examples of monomers of this type comprise styrene and vinyl chloride.

The oil phase may further contain an emulsifier used for stabilizing the HIPE. Emulsifiers used in a HIPE can include: (a) sorbitan monoesters of branched C16-C24 fatty acids; linear unsaturated C16-C22 fatty acids; and linear saturated C12-C14 fatty acids, such as sorbitan monooleate, sorbitan monomyristate, and sorbitan monoesters, sorbitan monolaurate diglycerol monooleate (DGMO), polyglycerol monoisostearate (PGMIS), and polyglycerol monomyristate (PGMM); (b) polyglycerol monoesters of—branched C16-C24 fatty acids, linear unsaturated C16-C22 fatty acids, or linear saturated C12-C14 fatty acids, such as diglycerol monooleate (for example diglycerol monoesters of C18:1 fatty acids), diglycerol monomyristate, diglycerol monoisostearate, and diglycerol monoesters; (c) diglycerol monoaliphatic ethers of—branched C16-C24 alcohols, linear unsaturated C16-C22 alcohols, and linear saturated C12-C14 alcohols, and mixtures of these emulsifiers. See U.S. Pat. Nos. 5,287,207 and 5,500,451. Another emulsifier that may be used is polyglycerol succinate (PGS), which is formed from an alkyl succinate, glycerol, and triglycerol.

Such emulsifiers, and combinations thereof, may be added to the oil phase so that they comprise between about 1% and about 20%, in certain examples from about 2% to about 15%, and in certain other examples from about 3% to about 12% by weight of the oil phase In certain examples, coemulsifiers may also be used to provide additional control of cell size, cell size distribution, and emulsion stability, particularly at higher temperatures, for example greater than about 65° C. Examples of coemulsifiers include phosphatidyl cholines and phosphatidyl choline-containing compositions, aliphatic betaines, long chain C12-C22 dialiphatic quaternary ammonium salts, short chain C1-C4 dialiphatic quaternary ammonium salts, long chain C12-C22 dialkoyl(alkenoyl)-2-hydroxyethyl, short chain C1-C4 dialiphatic quaternary ammonium salts, long chain C12-C22 dialiphatic imidazolinium quaternary ammonium salts, short chain C1-C4 dialiphatic imidazolinium quaternary ammonium salts, long chain C12-C22 monoaliphatic benzyl quaternary ammonium salts, long chain C12-C22 dialkoyl(alkenoyl)-2-aminoethyl, short chain C1-C4 monoaliphatic benzyl quaternary ammonium salts, short chain C1-C4 monohydroxyaliphatic quaternary ammonium salts. In certain examples, ditallow dimethyl ammonium methyl sulfate (DTDMAMS) may be used as a coemulsifier.

Photoinitiators may comprise between about 0.05% and about 10%, and in certain examples between about 0.2% and about 10% by weight of the oil phase. Lower amounts of photoinitiator allow light to better penetrate the HIPE foam, which can provide for polymerization deeper into the HIPE foam. However, if polymerization is done in an oxygen-containing environment, there should be enough photoinitiator to initiate the polymerization and overcome oxygen inhibition. Photoinitiators can respond rapidly and efficiently to a light source with the production of radicals, cations, and other species that are capable of initiating a polymerization reaction. The photoinitiators used in forming foams within contemplation of the present disclosure may absorb UV light at wavelengths of about 200 nanometers (nm) to about 800 nm, in certain examples about 250 nm to about 450 nm. If the photoinitiator is in the oil phase, suitable types of oil-soluble photoinitiators include benzyl ketals, α-hydroxyalkyl phenones, α-amino alkyl phenones, and acylphospine oxides. Examples of photoinitiators include 2,4,6-[trimethylbenzoyldiphosphine]oxide in combination with 2-hydroxy-2-methyl-1-phenylpropan-1-one (50:50 blend of the two is sold by Ciba Specialty Chemicals, Ludwigshafen, Germany as DAROCUR 4265); benzyl dimethyl ketal (sold by Ciba Geigy as IRGACURE 651); α-,α-dimethoxy-α-hydroxy acetophenone (sold by Ciba Specialty Chemicals as DAROCUR 1173); 2-methyl-1-[4-(methyl thio)phenyl]-2-morpholino-propan-1-one (sold by Ciba Specialty Chemicals as IRGACURE 907); 1-hydroxy-cyclohexyl-phenyl ketone (sold by Ciba Specialty Chemicals as IRGACURE 184); bis(2,4,6-trimethylbenzoyl)-phenylphosphincoxide (sold by Ciba Specialty Chemicals as IRGACURE 819); diethoxyacetophenone, and 4-(2-hydroxycthoxy)phenyl-(2-hydroxy-2-methylpropyl)ketone (sold by Ciba Specialty Chemicals as IRGACURE 2959); and Oligo [2-hydroxy-2-methyl-1-[4-(1-methylvinyl)phenyl]propanone] (sold by Lamberti spa, Gallarate, Italy as ESACURE KIP EM).

The dispersed aqueous phase of a HIPE comprises water, and may also comprise one or more components, such as initiator, photoinitiator, or electrolyte, wherein in certain examples, the one or more components are at least partially water soluble.

One component of the aqueous phase may be a water-soluble electrolyte. The water phase may contain from about 0.2% to about 40%, in certain examples from about 2% to about 20%, by weight of the aqueous phase of a water-soluble electrolyte. The electrolyte minimizes the tendency of monomers, comonomers, and crosslinkers that are primarily oil soluble to also dissolve in the aqueous phase. Examples of electrolytes include chlorides or sulfates of alkaline earth metals such as calcium or magnesium and chlorides or sulfates of alkali earth metals such as sodium. Such electrolyte can include a buffering agent for the control of pH during the polymerization, including such inorganic counterions as phosphate, borate, and carbonate, and mixtures thereof. Water soluble monomers may also be used in the aqueous phase, examples being acrylic acid and vinyl acetate.

Another component that may be present in the aqueous phase is a water-soluble free-radical initiator. The initiator can be present at up to about 20 mole percent based on the total moles of polymerizable monomers present in the oil phase. In certain examples, the initiator is present in an amount of from about 0.001 to about 10 mole percent based on the total moles of polymerizable monomers in the oil phase. Suitable initiators include ammonium persulfate, sodium persulfate, potassium persulfate, 2,2'-azobis(N,N'-dimethylencisobutyramidine)dihydrochloride, azo initiators, redox couples like persulfate-bisulfate, persulfate-ascorbic acid, and other suitable redox initiators. In certain examples, to reduce the potential for premature polymerization which may clog the emulsification system, addition of the initiator to the monomer phase may be just after or near the end of emulsification.

Photoinitiators present in the aqueous phase may be at least partially water soluble and may comprise between about 0.05% and about 10%, and in certain examples between about 0.2% and about 10% by weight of the oil phase. Lower amounts of photoinitiator allow light to better penetrate the HIPE foam, which can provide for polymerization deeper into the HIPE foam. However, if polymerization is done in an oxygen-containing environment, there should be enough photoinitiator to initiate the polymerization and overcome oxygen inhibition. Photoinitiators can respond rapidly and efficiently to a light source with the production of radicals, cations, and other species that are capable of initiating a polymerization reaction. The photoinitiators used to form foams within contemplation of the present disclosure may absorb UV light at wavelengths of from about 200 nanometers (nm) to about 800 nm, in certain examples from about 200 nm to about 350 nm, and in certain examples from about 350 nm to about 450 nm. If the photoinitiator is in the aqueous phase, suitable types of water-soluble photoinitiators include benzophenones, benzils, and thioxanthones. Examples of photoinitiators include 2,2'-Azobis[2-(2-imidazolin-2-yl)propane]dihydrochloride; 2,2'-Azobis[2-(2-imidazolin-2-yl)propane]disulfate dehydrate; 2,2'-Azobis(1-imino-1-pyrrolidino-2-ethylpropane) dihydrochloride; 2,2'-Azobis[2-methyl-N-(2-hydroxyethyl) propionamide]; 2,2'-Azobis(2-methylpropionamidine) dihydrochloride; 2,2'-dicarboxymethoxydibenzalacetone, 4,4'-dicarboxymethoxydibenzalacetone, 4,4'-dicarboxymethoxydibenzalcyclohexanone, 4-dimethylamino-4'-carboxymethoxydibenzalacetone; and 4,4'-disulphoxymethoxydibenzalacetone. Other suitable photoinitiators that can be used are listed in U.S. Pat. No. 4,824,765.

In addition to the previously described components other components may be included in either the aqueous or oil phase of a HIPE. Examples include antioxidants, for example hindered phenolics, hindered amine light stabilizers; plasticizers, for example dioctyl phthalate, dinonyl sebacate; flame retardants, for example halogenated hydrocarbons, phosphates, borates, inorganic salts such as antimony trioxide or ammonium phosphate or magnesium hydroxide; dyes and pigments; fluorescers; filler particles, for example starch, titanium dioxide, carbon black, or calcium carbonate; fibers; chain transfer agents; odor absorbers, for example activated carbon particulates; dissolved polymers; dissolved oligomers; and the like.

HIPE foam is produced from the polymerization of the monomers comprising the continuous oil phase of a HIPE. In certain examples, a HIPE foam layer may have one or more sublayers, and may be either homogeneous or heterogeneous polymeric open-celled foams. Homogeneity and heterogeneity relate to distinct layers within the same HIPE foam, which are similar in the case of homogeneous HIPE foams or which differ in the case of heterogeneous HIPE foams. A heterogeneous HIPE foam may contain at least two distinct sublayers that differ with regard to their chemical composition, physical properties, or both; for example layers may differ with regard to one or more of foam density, polymer composition, specific surface area, or pore size (also referred to as cell size). For example, for a HIPE foam, if the difference relates to pore size, the average pore size in the respective sublayers may differ by at least about 20%, in certain examples by at least about 35%, and in still other examples by at least about 50%. In another example, if the differences in the sublayers of a HIPE foam layer relate to density, the densities of the layers may differ by at least about 20%, in certain examples by at least about 35%, and in still other examples by at least about 50%. For instance, if one layer of a HIPE foam has a density of 0.020 g/cc, another layer may have a density of at least about 0.024 g/cc or less than about 0.016 g/cc, in certain examples at least about 0.027 g/cc or less than about 0.013 g/cc, and in still other examples at least about 0.030 g/cc or less than about 0.010 g/cc. If the differences between the layers are related to the chemical composition of the HIPE or HIPE foam, the differences may reflect a relative amount difference in at least one monomer component, for example by at least about 20%, in certain examples by at least about 35%, and in still further examples by at least about 50%. For instance, if one sublayer of a HIPE or HIPE foam is composed of about 10% styrene in its formulation, another sublayer of the HIPE or HIPE foam may be composed of at least about 12%, and in certain examples of at least about 15%.

A HIPE foam layer structured to have distinct sublayers formed from differing HIPEs may provide a HIPE foam layer with a range of desired performance characteristics. For example, a HIPE foam absorbent layer comprising first and second foam sublayers, wherein a first wearer-facing sublayer has a relatively larger pore or cell size, than the second sublayer, may more quickly absorb incoming fluids than the second sublayer. The first foam sublayer may be overlaid and be adjacent/continuous with or otherwise in contact with the second foam sublayer having relatively smaller pore sizes, and the second sublayer which exert greater capillary pressure and draw the acquired fluid from the first foam sublayer, restoring the first foam sublayer's ability to acquire more fluid. HIPE foam pore sizes may range from 1 to 200 μm and in certain examples may be less than 100 μm. HIPE foam layers of the present disclosure having two major parallel surfaces may be from about 0.5 to about 10 mm thick, and in certain examples from about 2 to about 10 mm. The desired thickness of a HIPE foam layer will depend on the materials used to form the HIPE foam layer, the speed at which a HIPE is deposited on a belt, and the intended use of the resulting HIPE foam layer.

The HIPE foam layers of the present disclosure may be manufactured to be relatively open-celled. This refers to a structure in which the individual cells or pores of the HIPE foam layer are in substantially unobstructed communication with adjoining cells. The cells in such substantially open-celled HIPE foam structures have intercellular openings or windows that are large enough to permit ready fluid transfer from one cell to its adjacent cells within the HIPE foam structure. For purpose of the present disclosure, a HIPE foam is considered "open-celled" if at least about 80% of the cells in the HIPE foam that are at least 1 μm in size are in fluid communication with at least one adjoining cell.

In addition to being open-celled, in certain examples HIPE foams are sufficiently hydrophilic to permit the HIPE foam to absorb aqueous fluids, for example the internal surfaces of a HIPE foam may be rendered hydrophilic by residual hydrophilizing surfactants or salts left in the HIPE foam following polymerization, by selected post-polymerization HIPE foam treatment procedures (as described hereafter), or combinations of both.

In certain examples, for example when used to form an absorbent layer, a HIPE foam layer may be flexible and exhibit an appropriate glass transition temperature (Tg). The Tg represents the midpoint of the transition between the glassy and rubbery states of the polymer. In general, HIPE foams that have a higher Tg than the temperature of use can be suitably strong but will also be relatively rigid and potentially prone to fracture. In certain examples, regions of the HIPE foams of the current disclosure which exhibit either a relatively high Tg or excessive brittleness will be discontinuous. Since these discontinuous regions will also generally exhibit high strength, they can be prepared at lower densities without compromising the overall strength of the HIPE foam.

HIPE foams intended for applications requiring flexibility should contain at least one continuous region having a Tg as low as possible, so long as the overall HIPE foam has acceptable strength at in-use temperatures. In certain examples, the Tg of this region will be less than about 40° C. for foams used at about ambient temperature conditions, in certain other examples less than about 30° C. For HIPE foams used in applications wherein the use temperature is higher or lower than ambient, the Tg of the continuous region may be no more than 10° C. greater than the use temperature, in certain examples the same as use temperature, and in further examples about 10° C. less than use temperature wherein flexibility is desired. Accordingly, monomers are selected as much as possible that provide corresponding polymers having lower Tg's.

HIPE foams useful for forming absorbent layers and/or sublayers within contemplation of the present disclosure, and methods for their manufacture, also include but are not necessarily limited to those foams and methods described in U.S. Pat. Nos. 10,045,890; 9,056,412; 8,629,192; 8,257,787; 7,393,878; 6,551,295; 6,525,106; 6,550,960; 6,406,648; 6,376,565; 6,372,953; 6,369,121; 6,365,642; 6,207,724; 6,204,298; 6,158,144; 6,107,538; 6,107,356; 6,083,211; 6,013,589; 5,899,893; 5,873,869; 5,863,958; 5,849,805; 5,827,909; 5,827,253; 5,817,704; 5,817,081; 5,795,921; 5,741,581; 5,652,194; 5,650,222; 5,632,737; 5,563,179; 5,550,167; 5,500,451; 5,387,207; 5,352,711; 5,397,316; 5,331,015; 5,292,777; 5,268,224; 5,260,345; 5,250,576; 5,149,720; 5,147,345; and US 2005/0197414; US 2005/0197415; US 2011/0160326; US 2011/0159135; US 2011/0159206; US 2011/0160321; and US 2011/0160689.

As reflected in FIG. 1, the absorbent layer formed of HIPE foam may include one or more patterns of perforations 42, including at least a first pattern disposed within an expected discharge region overlying the intersection of longitudinal and lateral axes 100, 200 of the pad. Perforations 42 may be punched, cut or otherwise formed through the entire z-direction depth of the HIPE foam absorbent layer, or only through a wearer-facing layer or partially into the wearer-facing portion thereof. When a HIPE foam absorbent layer is disposed directly beneath a topsheet as described herein, with no intervening acquisition layer formed of another material, perforations 42 may serve as a group of reservoirs to receive, temporarily hold, and aid in distributing rapid discharges of relatively small quantities of menstrual fluid, until the HIPE foam has sufficient time to distribute and absorb the fluid via capillary action. Additionally, such perforations help decrease bending stiffness of the absorbent layer, which may help increase both comfort and foldability. A more detailed description of configurations of such perforations in combination with examples of suitable absorbent layers may be found in U.S. Pat. No. 8,211,078.

Backsheet

The backsheet 30 may be positioned adjacent an outward-facing surface of the absorbent layer 40 and may be joined thereto by any suitable attachment methods. For example, the backsheet 30 may be secured to the absorbent layer 40 by a uniform continuous layer of adhesive, a patterned layer of adhesive, or an array of separate lines, spirals, or spots of adhesive. Alternatively, the attachment method may include heat bonds, pressure bonds, ultrasonic bonds, dynamic mechanical bonds, or any other suitable attachment mechanisms or combinations thereof. In other examples, it is contemplated that the absorbent layer 40 is not joined directly to the backsheet 30.

The backsheet 30 may be impervious, or substantially impervious, to liquids (e.g., urine, menstrual fluid) and may be manufactured from a thin plastic film, although other flexible liquid impervious materials may also be used. As used herein, the term "flexible" refers to materials which are compliant and will readily conform to the general shape and contours of the human body. The backsheet 30 may prevent, or at least substantially inhibit, fluids absorbed and contained within the absorbent layer 40 from escaping and reaching articles of the wearer's clothing which may contact the pad 10 such as underpants and outer clothing. However, in some instances, the backsheet 30 may be made and/or adapted to permit vapor to escape from the absorbent layer 40 (i.e., the backsheet may be made to be breathable), while in other instances the backsheet 30 may be made so as not to permit vapors to escape (i.e., it may be made to be non-breathable). Thus, the backsheet 30 may comprise a polymeric film such as thermoplastic films of polyethylene or polypropylene. A suitable material for the backsheet 30 is a thermoplastic film having a thickness of from about 0.012 mm (0.5 mil) to about 0.051 mm (2.0 mils), for example. Any suitable backsheet known in the art may be utilized with the present invention.

Some suitable examples of backsheets are described in U.S. Pat. Nos. 5,885,265; 4,342,314; and 4,463,045. Suitable single layer breathable backsheets for use herein include those described for example in GB A 2184 389; GB A 2184 390; GB A 2184 391; U.S. Pat. Nos. 4,591,523, 3,989,867, 3,156,242; WO 97/24097; U.S. Pat. Nos. 6,623, 464; 6,664,439 and 6,436,508.

The backsheet may have two layers: a first layer comprising a vapor permeable aperture-formed film layer and a second layer comprising a breathable microporous film layer, as described in U.S. Pat. No. 6,462,251. Other suitable examples of dual or multi-layer breathable backsheets for use herein include those described in U.S. Pat. Nos. 3,881, 489, 4,341,216, 4,713,068, 4,818,600; EP 203 821, EP 710 471; EP 710 472, and EP 0 793 952.

Folding

Referring to FIGS. 1, 3 and 4A-4C, a particular folding arrangement for the pad, to be placed inside an individual package, may be employed. This folding arrangement can be facilitated in some circumstances by construction of a thin pad utilizing an open-cell foam HIPE material for the absorbent layer, as described above. Open-celled HIPE foam provides advantages that include a thin and highly foldable but still suitably absorbent layer. It has been discovered that an absorbent layer of open-celled HIPE foam has greater resiliency and thereby enables a pad to take on less "set" from folding, than a pad having an absorbent layer of other absorbent materials that may cellulosic fiber and absorbent gelling material (or superabsorbent polymer material). Consequently, an absorbent layer formed of HIPE foam will more easily and completely return toward its open, flattened configuration following unpackaging and unfolding. It has been learned that this feature is desired by users because it reduces effort needed to manipulate the pad for positioning within the underpants. Further, the resiliency of the absorbent layer and the material forming it helps ensure that fluid transfer within the absorbent layer and along its length will be less likely to be interrupted or obstructed by permanently compressed/deformed regions created by folding, along the fold lines.

It has been learned, further, that this folding arrangement may be further facilitated and improved by the two-layer HIPE foam structure described above (and pictured in FIG. 2B, with a relatively larger-celled wearer-facing layer 40*a* and a relatively smaller-celled outward-facing layer 40*b*). Without intending to be bound by theory, it is believed that a relatively smaller-celled HIPE foam in an outward-facing layer 40*b*, having a greater number and density of cell walls and struts, has greater tensile strength needed to withstand the stress imposed on the outsides of the lateral folds (as described below) without substantial damage, while the relatively larger-celled wearer-facing layer 40*a*, having a lesser number and density of cell walls and struts, has greater compressibility and is more amenable to being compressed on the insides of the lateral folds. In other examples, an absorbent structure formed of or including a heterogeneous mass or layer assembly that includes a combination of relatively open-celled foam, such as but not limited to HIPE foam, in one or a plurality of discrete sections or pieces, layered and/or intermingled with fibers of a nonwoven web such that these components are present in a singularized layer, may provide a highly flexible, thin, foldable absorbent structure that substantially retains its fluid distribution and absorbency properties despite being folded as described herein. Non-limiting examples of such layer assemblies and/or heterogeneous masses are described in, for example, U.S. application Ser. Nos. 14/704,110; 15/343,989; 15/344,050; 15/344,177; 15/344,239; 15/344,255; 15/587,455; and Ser. No. 15/587,876; and U.S. App. Pub. No. US 2019/0269564.

As depicted in the figures, pad 10 may first be folded about side longitudinal fold lines 204, about which wings 15 are folded laterally over the wearer-facing surface of the pad. Following such folding, one or more suitably-sized section(s) of a thin release film or paper (not shown) may be laid over and applied to the portions of the wings having backsheet adhesive 35 deposited thereon, to cover the adhesive and protect it from unwanted sticking, until the time the user wishes to apply the pad to her underpants. To avoid unnecessarily adding caliper to the pad in the completely folded configuration, it may be desired to avoid folding the pad along any longitudinal fold lines that traverse the absorbent layer or polymeric foam material included in the absorbent layer. As noted above, the central outward-facing surfaces of the pad having backsheet adhesive 35 deposited thereon may also be covered with one or more sections of release film or paper (not shown).

After folding of the wings 15 about side longitudinal fold lines 204, the pad may be further folded into at least four sections including front section 210, front-mid section 211, rear-mid section 212 and rear section 213, along at least a front lateral fold line 201, middle lateral fold line 202 and rear lateral fold line 203. Middle lateral fold line 202 may, but does not necessarily have to, coincide with pad lateral axis 200. Sections 210, 211, 212 and 213 may be approximately equal in length, or the lengths of each (i.e., the positions of the lateral folding lines) may be adjusted to facilitate folding of one section length inside another section length.

Along lateral folding lines 201, 202 and 203, the pad may be folded into at least four sections 210, 211, 212 and 213 in a number of ways. However, for dual, but unrelated, purposes of (1) providing a folded pad configuration 10*a* with a singularized fold nose 214, and (2) minimizing folding damage to an absorbent layer formed of two layers of open-celled HIPE foam material as described above, one of two folding configurations may be applied.

Figure 4A:
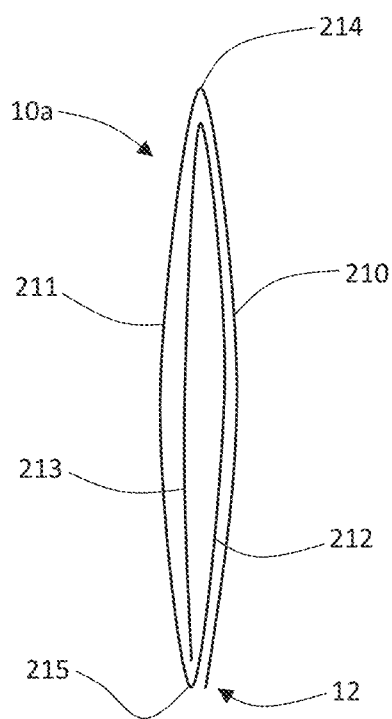
FIG. 4A is a schematic side view of a feminine hygiene pad folded in four sections in a roll fold configuration, with a main fold nose oriented toward the top of the figure.

The first is a "roll" fold configuration depicted in FIG. 4A. In a roll fold configuration, rear section 213 is folded along about rear lateral fold line 203 over rear-mid section 212; then both sections 213 and 212 together are folded about middle lateral fold line 202 over front-mid section 211; and lastly, the three section 213, 212 and 211 together are folded about front lateral fold line 201 over front section 210. The foregoing procedure results in a front-section-out roll fold configuration, in which front section 210 and forward end 12 are disposed on the outside of the folded pad configuration 10*a* as shown in FIG. 4A. It will be appreciated that an alternative roll fold configuration as described above may be formed by first folding the front section 210 over about front lateral fold line 201, and preceding to fold rearward, resulting in a rear-section-out roll fold configuration, in which rear section 210 and rearward end 14 lie on the outside of the folded configuration. A front-section-out roll fold configuration as shown in FIG. 4A may be desired, however, for purposes of user convenience, because it provides for front-to-rear unfolding that may be more intuitive for the user. It will be appreciated that a front-section-out roll fold configuration, or a rear-section-out roll fold configuration (if desired), may be created via steps that differ from those described above.

Figure 4B:
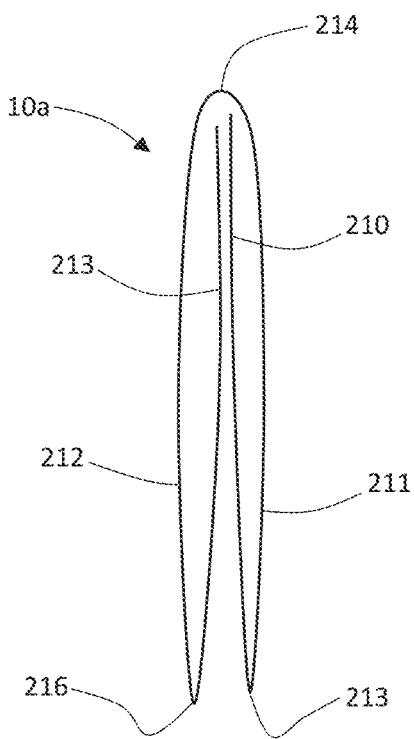
FIG. 4B is a schematic side view of a feminine hygiene pad folded in four section in a book jacket fold configuration, with a main fold nose oriented toward the top of the figure.
Figure 4C:
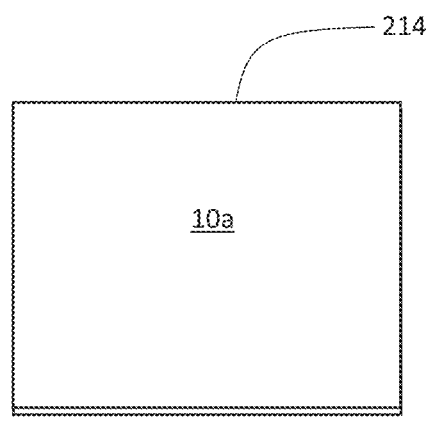
FIG. 4C is a schematic front view of a folded feminine hygiene pad, with a main fold nose oriented toward the top of the figure.
Figure 7:
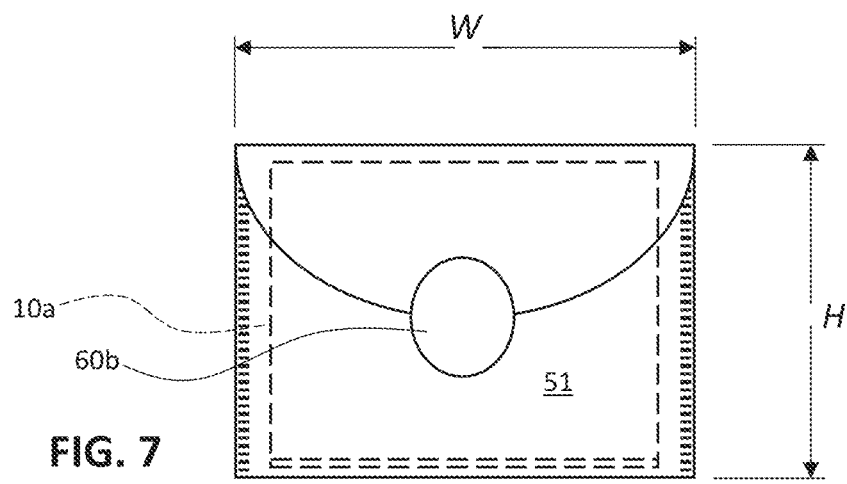
FIG. 7 is a front view of the closed envelope package as shown in FIG. 6A, showing positioning of a folded feminine hygiene pad within the package.

The second configuration is a "book jacket" fold configuration, named herein because it resembles the manner in which a book jacket (or book dust jacket) is folded, and is depicted in FIG. 4B. In a book jacket fold configuration, front section 210 is folded about front lateral fold line 201 over front-mid section 211; and rear second 212 is folded about rear lateral fold line 203 over rear-mid section 212 (these two folds can occur simultaneously or one after another in either order). Finally, the two remaining portions comprising front section 210 folded over front-mid section 211 as one portion, and rear section 213 folded over rear-mid section 212, are folded about middle lateral fold line 202 to bring them together to create the book jacket fold configuration depicted in FIG. 4B.

It will be appreciated that in both the roll and book jacket fold configurations depicted and described, in all folds about lateral fold lines 201, 202 and 203, the fold is formed with the wearer-facing (i.e., topsheet) surfaces facing inward in the fold. This serves three purposes. First, it is believed that it provides for more intuitive, and therefore more convenient, unfolding for the user. Second, it cooperates with an absorbent layer formed of two sublayers of open-celled HIPE foam, as described above, to help minimize permanent deformation, or damage, to the absorbent layer resulting from folding.

Third, it can be seen in FIGS. 4A and 4B that both the roll fold configuration and the book jacket fold configuration result in an isolated and singularized main fold nose 214, wherein an outside folded edge along one of the lateral fold lines is alone, with no proximate folded or end edges present—in contrast to the secondary fold nose 215 proximate to end edge 12 shown at the bottom of FIG. 4A and proximate secondary fold noses 216, 217 shown at the bottom of FIG. 4B). A singularized main fold nose 214 may be desired for purposes of user convenience and user perceptions of greater imperviousness to contamination of the product, as will be described below.

Package

Referring to FIGS. 5A, 5B, 6A, 6B, 7 and 8, for purposes of providing a package for an individual folded feminine hygiene pad that can be easily and quietly opened by a user, it may be desired to provide a package having some or all of the features depicted and described herein. Package 50 may have an envelope configuration as depicted. It may be formed from a single sheet of web material, preferably a nonwoven web material, polymeric film material, or laminate of a nonwoven web material and polymeric film material. The single sheet of material may be cut to appropriate length, size and shape configured to provide front panel 51, rear panel 53 and closure flap 58, wherein front panel 51 is cut to provide an extended access front opening edge 54 visible in an opened configuration shown in FIGS. 5A and 5B, and a closure flap 58 that may in some examples be configured to overlie and cover front opening edge 54 when in the closed configuration as shown in FIGS. 6A and 6B (flap 58 folded about closure flap fold line 56). The cut package material may be folded as shown and then ultrasonically, thermally, compressively and/or adhesively bonded alongside edges thereof to form side seams 52 and thereby form the envelope structure. In order to minimize the size of the package, it may be desired to minimize the margin of film material along the side scams that is present in the seams, and utilize a thermal bonding-fusion mechanism (e.g., by application of heat directly, or via ultrasonic means) that results in side seams formed of welded/fused film material that are no more than 6 mm in width, more preferably no more than 4 mm in width, and even more preferably no more than 3 mm in width.

Where the package includes a polymeric film material, it may be desired that the film material have properties that make it relatively quiet when handled or manipulated, for purposes of providing a discreet package. In some examples, the film material may comprise polyethylene. In some examples the polymer resin from which the film is formed may include a particle filler or additive, such as particles of calcium carbonate. Without intending to be bound by theory, it is believed that such particle fillers may beneficially reduce noise generation/transmission characteristics of the polymer film. Nonlimiting examples of suitable polymer film and particle filler compositions are disclosed in US 2015/0376384 and US 2015/0376383.

Many currently marketed feminine hygiene pads are individually packaged in packages that require the consumer to destructively tear the package along scams or through the package material itself, to access the pad within. Such destructive opening creates the potential to generate, or actually generates, unwanted noise during package opening. In order to further minimize noise created by opening of the package, and to preserve the package structure so it can be used to receive and hold a used pad for later disposal, it may be desired that the package be configured so that it can be opened without substantial destruction thereto. In some examples, the packaging may be configured such that accessing the pad within requires separating the package material along a total/combined distance of no more than 50 percent of the total length of all seams present, more preferably no more than 30 percent of the total length of all seams present, and even more preferably no more than 15 percent of the total length of all scams present.

In some examples, an openable closure element may be provided, in combination with any of the other package features described herein. In some examples a closure element may include a releasable flap closure adhesive 60a on the underside of the flap 58, or panel closure adhesive 60c on the outside of the package front panel 51, and in some examples may include an adhesive closure tape or sticker 60b that overlies the edge of closure flap 58 and adheres to the front panel 51 of package 50. In some examples the closure element may be a deposit of releasable closure adhesive 60a (e.g., in a position as depicted in FIG. 5A) alone, applied to the underside of flap 58 in a suitable position and shape to adhere the flap to front panel 51 without contacting a pad contained in the package. Such adhesive may be applied in a position on the flap so as to be present along most or substantially the entire opening edge 54 when the flap 58 is closed (i.e., extending substantially along the flap edge and/or opening edge 54 from one side seam 52 to the other), to make a more complete closure that reduces chances of contamination of a new pad within the package. In some examples a deposit of releasable panel closure adhesive 60c may be disposed on the front panel 51, which may be desired to minimize likelihood of inadvertent contact with the pad. In some examples the releasable adhesive may also be reusable/refastenable, which may make the package 50 more useful for storing a used pad for disposal.

In some examples such as depicted in FIGS. 9A, 9B, 10A and 10B, an envelope package may be formed about a pad in a flow-wrap process in which a seam 55 is created in back panel 53. As depicted in FIGS. 9B and 10B, scam 55 is a fin seam; however, scam 55 may also be in the form of an overlap seam that lies flush along the rear panel 53. Either a fin seam or an overlap seam may be formed and held together via thermal bonding/fusion of the separate portions of film joined therealong, by a deposit of a suitable adhesive between the separate portions of film, or a combination thereof. In some examples it may be desired that attachment between the joined sections forming back panel 53, at seam 55, whether effected by adhesive or by welding/fusion, be intermittent or discontinuous and may have spaced intervals of attachment, rather than being continuous, along seam 55. This may be desired to allow venting of air from the finished package upon compression of the package, such as may occur in processes downstream of package formation, reducing chances that the package will burst open along scams or along the flap closure.

Still referring to FIGS. 9A, 9B, 10A and 10B, rather than be separate of film forming front panel 51, flap 58 may be contiguous and integral with film forming front panel 51, and may be defined along edge 54 by a path of perforations, laser scoring, mechanical scoring or cutting or other suitable mechanism for imparting a path of separation along which front panel 51 and flap 58 will easily tear away or separate from each other. A larger flap sticker 60d with flap sticker adhesive 60e disposed to hold it to the front panel 51 and flap 58 may overlie the path of separation and thereby prevent opening of the package until desired by the user. When the user wishes to open the package, she may lift and peal the flap sticker 60d upwardly, and the adhered flap sticker 60d will pull the flap 58 along therewith, causing the front panel 51 and flap 58 to separate along the path of separation to create access opening edge 54. In some examples the film forming front panel 51 may be cut (such as by die-cutting) substantially entirely through its thickness along the path of separation during the manufacturing/packaging process, following application of flap sticker 60d to the package film, such that the flap sticker 60d and flap sticker adhesive 60e thereunder are the only structure that effectively holds the flap in a closed position after packaging is completed. This may provide for a particularly quiet flap opening experience for the user, when a suitable flap sticker adhesive composition is included, because the user will not need to tear the film of the front panel (which has a potential to generate noise) to open the package. In some examples it may be desired that the flap sticker be of a size and shape suitable to cover the entirety of the path of separation. Such a feature may serve to enhance the ability of the package to protect a new pad from contamination prior to use; to create favorable consumer perceptions resulting from such effect; and to make the package a more effective container/disposal aid for receiving, isolating and carrying a used pad until the time the user can dispose of it.

Figure 10C:
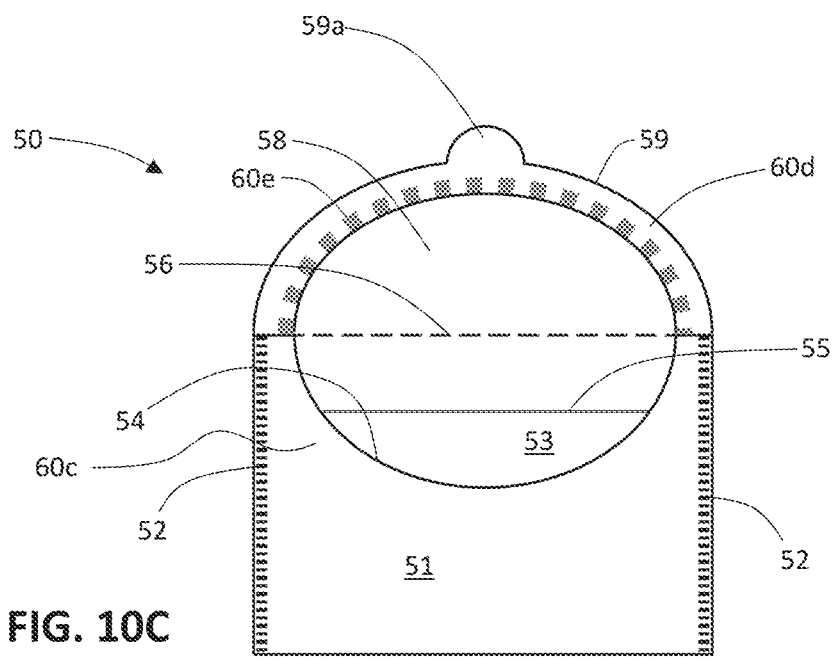
FIG. 10C is a front view of an another example of an envelope package in an opened configuration.
Figure 10D:
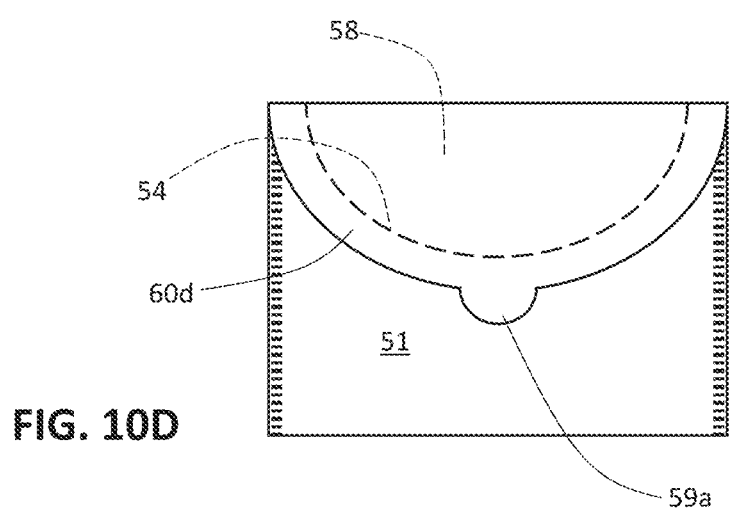
FIG. 10D is a front view of an another example of an envelope package in a closed configuration.

As may be appreciated from FIGS. 10C and 10D, in some examples a flap sticker 60d may include a lift tab 59. Lift tab 59 may simply be an extension of the distal end of flap sticker 60d. Lift tab 59 or a distal portion thereof may be provided with a reduced amount, or entirely without, any adhesive 60c thereon. In such configuration, lift tab 59 may easily be lifted away from front panel 51 and grasped by the consumer, facilitating the consumer's lifting and peeling upward of flap sticker 60d and/or flap 58 to open the package.

It will be appreciated that a package configuration such as any of those depicted in FIGS. 5A, 5B, 6A, 6B, 7, 8, 9A, 9B, 10A-10D and described herein, may be configured so as to be openable with substantially limited or even no destruction thereto, and to be recloseable, so as to make it suitable to serve as a disposal aid-into which the user may insert a used, folded pad, and reclose the package around it, to isolate the used pad until a convenient time for disposal thereof. Where an openable flap 58 is provided, it may be configured to be openable without substantial destruction of the flap itself, and without substantial destruction or separations of other portions of the package (e.g. side seams 52), such that the flap is effectively recloseable to cover the access opening. Additionally, a reclosure refastenability feature may be provided, such as, for example a releaseable/refastenable flap closure adhesive 60a beneath the flap or a releasable/refastenable adhesive 60e beneath a flap sticker 60b or 60d, such that the flap 58 and access opening may be fastenably reclosed after opening.

As may be appreciated from the figures, in some examples it may be desired that the opening edge 54 follow a curving path, which will avoid localization of stresses therealong and thereby avoid unintended tearing of the package film. In some examples it may be desired that the curving path be configured such that a greatest portion of the contained folded pad is exposed and made accessible to the user at a location between the side seams 52, for purposes of user convenience.

It may be desired that the package 50 be sized relative the folded pad 10a, so as to be as small as possible (for convenient and discreet carry) without being so snug as to create friction between the folded pad 10a and the insides of the package sufficient to frustrate easy and quiet withdrawal of the pad from the package. Similarly, and also for purposes of nondestructive and easy withdrawal of the pad from the package, it may be desired that the folded pad 10a and the package 50 be configured such that there are few or no substantial deposits of adhesive, preferably no deposits of adhesive, disposed between the outside surfaces of the folded pad 10a and the inside surfaces of the package 50 and/or the closure flap 58.

Through prototyping, it has been discovered that a normal-capacity daytime use feminine hygiene pad of the same design and materials as current ALWAYS INFINITY pads (a product of The Procter & Gamble Company, Cincinnati, Ohio) and having an absorbent layer formed of an open-celled HIPE foam, can be folded and packaged as described herein to have an uncompressed package caliper when laid flat on a horizontal surface of 25 mm or less, more preferably 20 mm or less, even more preferably 15 mm or less, or from 10 mm to 25 mm, more preferably from 10 mm to 20 mm, and even more preferably from 10 mm to 15 mm-following removal from a larger package containing a plurality of individually packaged pads, and a 24-hour rest period. This package caliper contributes to providing a relatively small packaged pad believed to be preferred by many consumers for its discreet pocketability and case of discreet one-hand carry.

It has been discovered that, between packages that are square or nearly square in shape (aspect ratio of package height to width of approximately 1.0) and packages that are rectangular but not square in shape, consumers prefer the non-square packages, for reasons that are not thoroughly understood but are believed to relate to perceived convenience of pocketability and/or discreet carry. Accordingly, it may be desired to configure the pad and the package such that the closed package with the contained pad is rectangular in shape and has an aspect ratio of height H to width W (see FIGS. 7) of 0.40 to 0.95, more preferably 0.45 to 0.85, and even more preferably 0.50 to 0.75.

Figure 8:
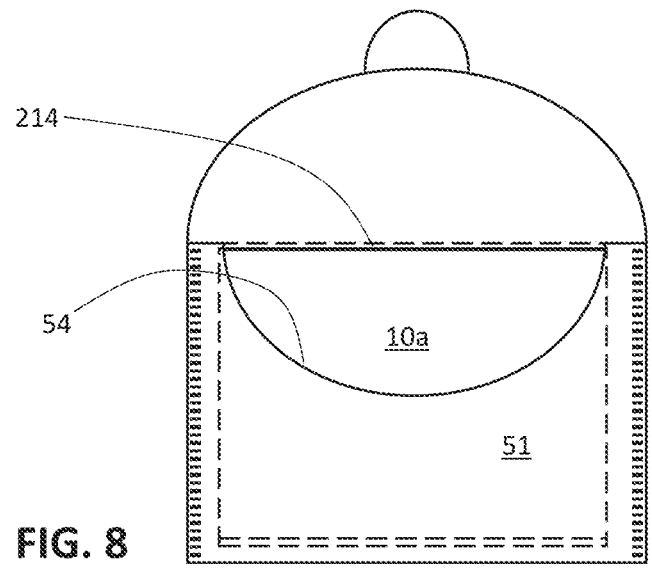
FIG. 8 is a front view of the closed envelope package as shown in FIG. 5A, showing positioning of a folded feminine hygiene pad within the package.

In order to maximize user convenience, it may be desired that a folded pad 10a, folded as described above, be placed within the package with a main fold nose 214 disposed closest the package opening or top of the package (when the package is in an opened configuration) as suggested in FIG. 8. Placing a main fold nose 214 relative the package opening in this orientation presents the user with a single edge of the folded product that she can quickly and easily visually and/or tactilely identify, for easy and quick grasping of the entire pad, e.g., between a thumb and forefinger, and removal from the package. By contrast, when multiple edges of the folded pad are presented in the opening, user effort grasping and removing the pad from the package may require more slightly more concentration and/or effort. It has been discovered that users substantially prefer the former configuration, for this reason, and also for the reason that users perceive that this configuration of the pad within the package makes the pad more impervious to contamination.

Another feature that may be desired to improve user convenience is to impart contrasting colors or other visible characteristics to the respective outside visible surfaces of the folded pad 10a and the inside surfaces of the package material, thereby providing a visual contrast between the inside surfaces of the opened package and an outer surface of the pad as contained therein, visible immediately after the package is opened. This feature helps the user quickly visually identify the pad within the package for grasping and removal. Visual contrast may be imparted by any suitable techniques including tinting, pigmenting or printing the materials of the pad backsheet, the release film or paper, the package material, or any combination thereof. Herein, a "visual contrast" between colors or shades of two respective materials means that an ordinary observer having 20/20 vision (natural or corrected) and no substantial color vision deficiency, in normal office lighting conditions appropriate for desktop work, can perceive a contrast between the color(s) on the outside of the folded pad in the package, and the color(s) of the inside of the package material, with the package in an opened condition. Alternatively, for relatively close colors or shades, a "visual contrast" is identified when the value of delta E* determined through the Visual Contrast method below is equal to or greater than 2.0. For enhanced visual contrast, it may be preferred that the value of delta E* be equal to or greater than 3.5. Alternatively, where decorative designs are visibly present on one or both the outside of the folded pad as contained in the package, and the inside of the package material with the package in opened configuration, a "visual contrast" is identified when a design is visibly present on one but not the other, or when designs are visibly present on each but the designs differ in any visible respect.

Process

Figure 11A:
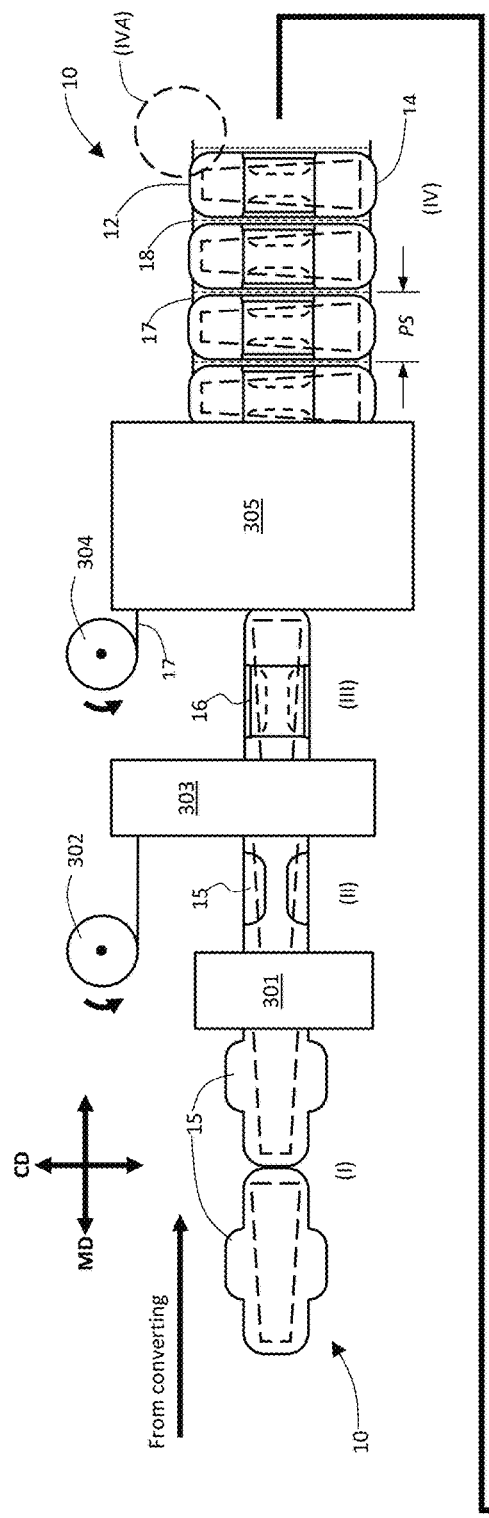
FIG. 11A is a schematic plan view depiction of an example of process flow for finishing and packaging feminine hygiene pads.
Figure 11A:
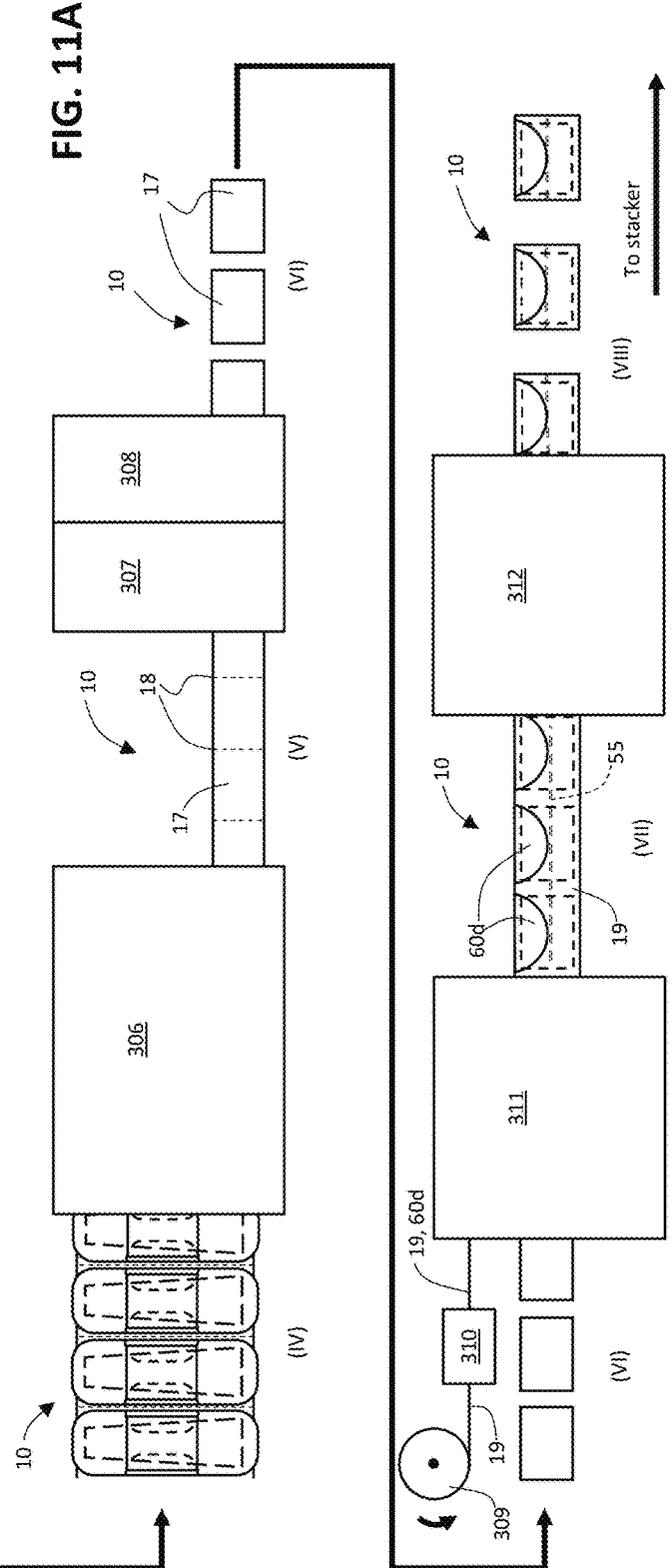

It has been learned that one or more of the process steps described below may be advantageous for imparting product features described above, and may provide additional advantages in manufacturing efficiency, reliability and quality assurance. Referring now to FIG. 11A, a process for manufacturing a packaged, folded feminine hygiene article is schematically depicted.

Starting at the top left of the figure, feminine hygiene pads 10 may be received from a converting line in configuration (I) in substantially finished condition, and with their longitudinal axes oriented in the machine direction MD. At the beginning of the process, pads 10 may have yet to have had backsheet adhesive 35 (see FIGS. 2A, 2B and 3) applied. Pads 10 may include wings 15, as previously described. Pads 10 may be conveyed from the converting line to a wing folding unit 301, which folds wings 15 (along, e.g., side longitudinal fold lines 204, see FIG. 1) over the wearer-facing/topsheet surfaces of the pads 10, from which they emerge in configuration (II) with the wings 15 folded over. (A more detailed example of a depiction of a pad as it would appear in configuration (II) appears in FIG. 3.)

In configuration (II), the pads may be conveyed to a wings coversheet application unit 303. The wings coversheet application unit 303 may be configured to receive wings coversheet stock from a supply roll 302 (which may be a roll of polymeric film or paper bearing an adhesive release surface or coating), cut it into individual wings coversheets 16, apply deposits of backsheet adhesive thereto, and place the individual wings coversheets 16 bearing the adhesive over the folded wings 15. Upon contact between the wings coversheet 16 and the folded over, outward-facing surfaces of the wings, the adhesive applied to the wings coversheet 16 can adhere and effectively transfer to the wings, so as to become a first portion of backsheet adhesive 35 deposited on the wings (see, e.g., FIGS. 2A and 3) and later remain in place on the wings when a user peels away the coversheet 16 in preparation to apply the pad to underwear. Prior to use, the wings coversheet 16 may serve to cover the adhesive and prevent it from being contaminated or adhering to surfaces not intended by the user. In some examples, the process may be configured to apply the adhesive directly to the wings directly/initially, rather than to the wings coversheets 16. The process can be configured such that the pads emerge from wings coversheet application unit 303 in configuration (III).

In configuration (III), the pads may be conveyed to a turn and repitch unit 305. Unit 305 may be a single unit, or a combination of cooperating units configured to receive individual pads moving with their longitudinal axes oriented in the machine direction MD, rotate them 90 degrees such that their longitudinal axes are oriented in the cross direction CD, phase them (i.e., space them along the MD by a predetermined distance), and place them onto a continuous web of backsheet adhesive coversheet stock 17. Unit 305 may also be configured to receive backsheet adhesive coversheet stock 17 from a supply roll 304 and place the rotated pads thereonto. Unit 305 may also be configured to apply a deposit of backsheet adhesive, either directly to the pads, or indirectly to the backsheet adhesive coversheet 17 stock, such that the adhesive applied to the backsheet coversheets can adhere and effectively transfer to outward-facing surfaces of the pads (e.g., the outward-facing surfaces of the pad backsheets), so as to become a second portion of backsheet adhesive 35 deposited on the pads (see, e.g., FIGS. 2A and 3) and later remain in place on the pads when a user peels away the backsheet adhesive coversheet 17 in preparation to apply the pad to underwear.

Backsheet adhesive coversheet stock 17 may be any polymeric film or paper material suitable for serving as a releasable coversheet for covering areas of the pad bearing backsheet adhesive 35. Further, in many circumstances, it may be desired that coversheet stock 17 be a material that is quiet, i.e., does not generate substantial audible noise, when manipulated by a user (such as when she removes the backsheet adhesive coversheet 17a from the pad in preparation to apply the pad to underwear). For this reason, a relatively quiet polymeric film may be selected for the coversheet stock 17. In some examples the film may be predominately polyethylene, of an average caliper no greater than 0.08 mm (80 µm), preferably no greater than 0.065 mm (65 µm) and even more preferably no greater than 0.05 mm (50 µm). Polyethylene-based films tend to be relatively quiet as compared with paper and with films based on other polymers. Other relatively quiet film materials might also be selected.

Backsheet adhesive coversheet stock 17 may be provided on the supply roll 304 with machine-direction-spaced separation perforations 18 already present, or alternatively, unit 305 may include a perforation unit (not specifically shown) that provides successive cross-direction lines of separation perforations 18 (or other suitable lines of weakness, such as scoring partially through the thickness of the backsheet adhesive coversheet stock), substantially uniformly spaced along the machine direction by distances approximately corresponding to the widths of the pads with wings folded. Spacing PS of separation perforations 18 along the coversheet stock 17 may include any desired margins beyond the pad widths, but in some circumstances, it may be desired that such margins be minimized for purposes of compactness and neatness of the completed folded pad product. Thus, in some examples it may be desired that machine-direction spacing PS of separation perforations 18 be no greater than 125 percent of the average width of the pads (wings, if present, folded), more preferably no greater than 120 percent of the average width of the pads, and even more preferably no greater than 115 percent of the average width of the pads. As a result, following completion according to the further process steps described below, the widths of the backsheet adhesive coversheets on the pad products will be, respectively, no greater than 125 percent of the average width of the pads (wings, if present, folded), more preferably no greater than 120 percent of the average width of the pads, and even more preferably no greater than 115 percent of the average width of the pads. It will be appreciated, however, that as a feature or result of the process steps described herein, in no case will the machine-direction spacing PS be less than 100 percent of the average width of the pads.

Additionally, in FIG. 11A, it can be observed that the individually oriented, spaced series of pads 10b in configuration (IV) may have, between them prior to folding, separation perforations 18 in the backsheet adhesive coversheet stock 17. It may be appreciated that the above-described method and any variant thereof, that successively places pads 10 on backsheet coversheet stock with the pads' longitudinal axes oriented in the cross direction CD, enables the manufacturer to provide coversheet stock 17 having a cross-direction dimension that is less than the length ($L_P$, see FIG. 3) of the pads. To illustrate, referring to location (IVA) of FIG. 11A, it can be seen that coversheet stock 17 does not extend in the cross direction CD to the ends 12, 14 of the pads, but rather, lies short of them. This feature of the process is another way to enable the manufacturer to provide for a smaller, neater folded pad configuration because no unused margins of coversheet stock material 17 extend past the ends 12, 14 of the pads.

In configuration (IV), the series of pads 10b with adhered backsheet adhesive coversheet stock 17 may be conveyed to a folding unit 306. Folding unit 306 may be configured to continuously fold the series of pads 10b into two, three, four or more sections (for example, along fold lines 201, 202, 203, 204; see FIGS. 3, 4A and 4B), resulting in a connected series of folded pads 10c (adhered to backsheet adhesive coversheet stock 17), in configuration (V). Folding unit 306 may be configured such that in configuration (V), the connected series of folded pads 10c are imparted with, for example, one of the folding configurations schematically illustrated in FIGS. 4A and 4B.

In configuration (V), the connected series of folded pads 10c may be conveyed to a separation unit 307. Separation unit 307 may be configured to continuously and successively exert machine direction tensile force on the successive pads, perpendicular to and across the lines of the separation perforations 18, causing the backsheet adhesive coversheet stock 17 to separate along the perforations 18. This results in a series of separated, folded pads 10a, each of which includes a backsheet adhesive coversheet 17a. Following separation, the folded, separated pads may be conveyed to a packaging phasing unit 308 configured to space the folded pads apart from one another along the machine direction, by a predetermined distance suitably selected for individual packaging as will be described below.

Figure 12:
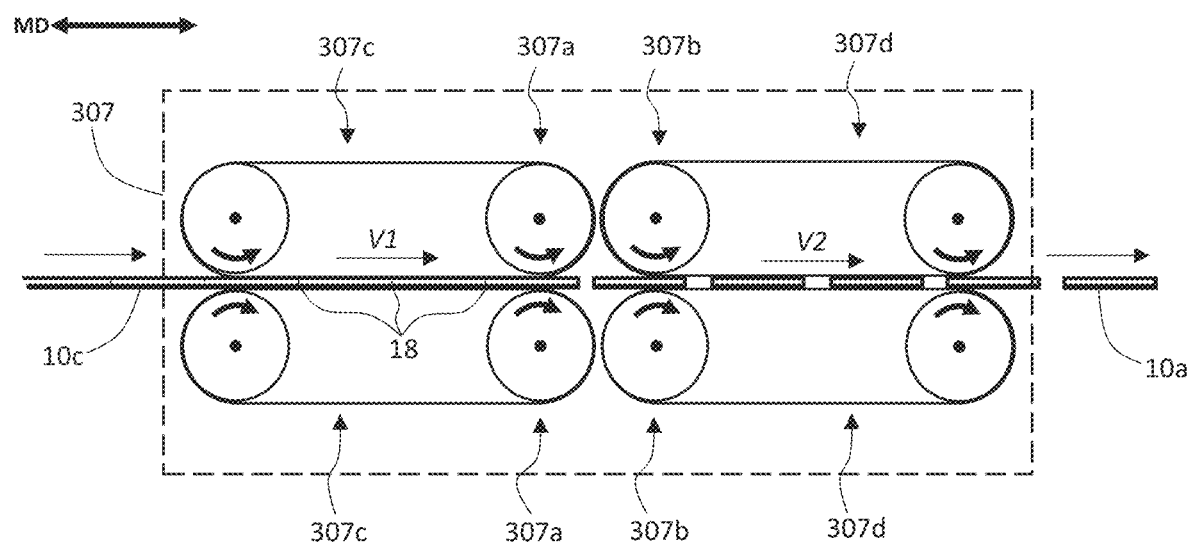
FIG. 12 is a schematic side view depiction of operating components of an example of a separation unit, shown operating with a series of folded pads.

In some examples, referring to FIG. 12, separation unit 307 may include two successive pairs of opposing separation rollers including an upstream pair 307a and a downstream pair 307b. Each respective pair of separation rollers 307a, 307b may be configured to operate without conveyor belts (whereby the pads 10c, 10a pass directly through the nip between each pair of rollers), or with respective corresponding, respective upstream and downstream pairs of upper and lower conveyor belts 307c, 307d cycling about each of the rollers (whereby the pads pass between the respective upper and lower belts). Upstream separation roller pair 307a may be operated such that their circumferential roller surfaces move at a tangential/linear velocity V1. Downstream separation roller pair 307b may be operated such that their circumferential roller surfaces move at a tangential/linear velocity V2. To effect separation of successive pads, the system may be configured and operated such that V2 is greater than V1. As each connected pad in the series 10c emerges from the nip or space between pair 307a and enters the nip or space between pair 307b moving at a greater velocity, friction between the pad and pair 307b, or between the pad and belts 307d, increases machine direction tension in the pad between roller pairs 307a, 307b, and causes each, leading, exiting folded pad 10a to separate from the incoming/trailing series of pads 10c, along the separation perforations 18.

From the foregoing description it will be appreciated that the average width of the backsheet adhesive coversheets 17a on the separated folded pads 10a will be approximately equal to the spacing PS between the separation perforations 18 as shown in FIG. 11B. Thus, according to the description above, it may be desired that average width of the adhesive coversheets 17a be less than 125 percent, more preferably less than 120 percent, and even more preferably less than 115 percent (and in all cases at least 100 percent) of the width of the pads. For purposes of identifying presence of this feature and eliminating uncertainty resulting from variance in wing portion folding locations, the width of a pad is the greatest width of any portion of the absorbent layer 40 or absorbent core component disposed between the topsheet and backsheet. For purposes herein, averages may be calculated after measurements of adhesive backsheet coversheets and absorbent layer/core components of 10 examples of the product in question.

In view of the foregoing process description, the configuration of the separation perforations 18 may be important to efficient operation of the process as well as appearance of the resulting product. It may be desired that the separation perforations 18 through the coversheet stock 17 are not so extensive as to unacceptably compromise the tensile strength of the coversheet stock 17, i.e., its ability to withstand ordinary machine direction operating tension in the line upstream of the separation unit 307. If the separation perforations 18 are too extensive, the coversheet stock 17 may be vulnerable to premature, unwanted separation in processes upstream of the separation unit 307, which can necessitate line shutdown. On the other hand, it may be desired that the coversheet stock separate easily, neatly and cleanly in separation unit 307, so as to provide for smooth, even and uninterrupted conveyance of the pads through the separation unit 307 and the remainder of the line downstream, and provide a neat finished appearance to the separated side edges of the individual backsheet adhesive coversheets 17a, such that the edges have a relatively smooth, not jagged appearance to the naked eye.

Figure 13A:
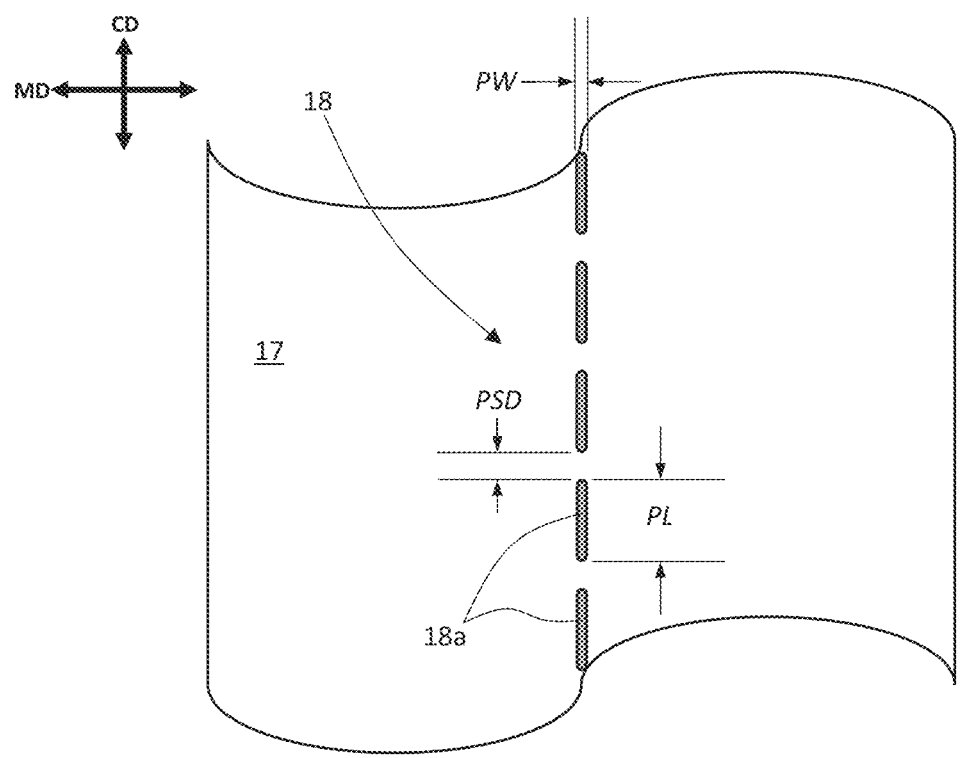
FIG. 13A is an expanded plan view depiction of a portion of backsheet adhesive coversheet supply web with separation perforations.

Referring to FIG. 13A, separation perforations 18 may be substantially uniformly dimensioned and spaced to provide for smooth and even separation. The perforations may be created mechanically, e.g., by use of a perforating die, or thermally, e.g., by use of a suitably selected and tuned laser. The perforations may penetrate the film entirely, or only partially, to an extent sufficient to propagate an orderly separation of the file along the perforations. Separation perforations 18 have an average length PL in the cross direction CD, an average separation distance PSD in the cross direction CD, and an average perforation width PW in the machine direction MD. For purposes of balancing the needs for preserving suitable tensile strength in coversheet stock 17 upstream of the separation unit 307, providing for efficient separation of pads in separation unit 307, and providing for backsheet adhesive coversheets 17a with neatly separated edges in the finished product, it may be desired to configure perforating equipment such that perforations 18 have the following ranges of dimensions and ratio:

average PL=0.4 mm to 3.5 mm; more preferably 0.45 mm to 2.0 mm; and even more preferably 0.5 mm to 1.0 mm;

average PSD=0.7 mm to 2.5 mm; more preferably 0.75 mm to 1.8 mm; and even more preferably 0.80 mm to 1.1 mm;

average PW=0.015 to 0.1 mm; and average PL/(average PL+average PSD)=0.15 to 0.70; more preferably 0.25 to 0.55; and even more preferably 0.30 to 0.50.

Figure 13B:
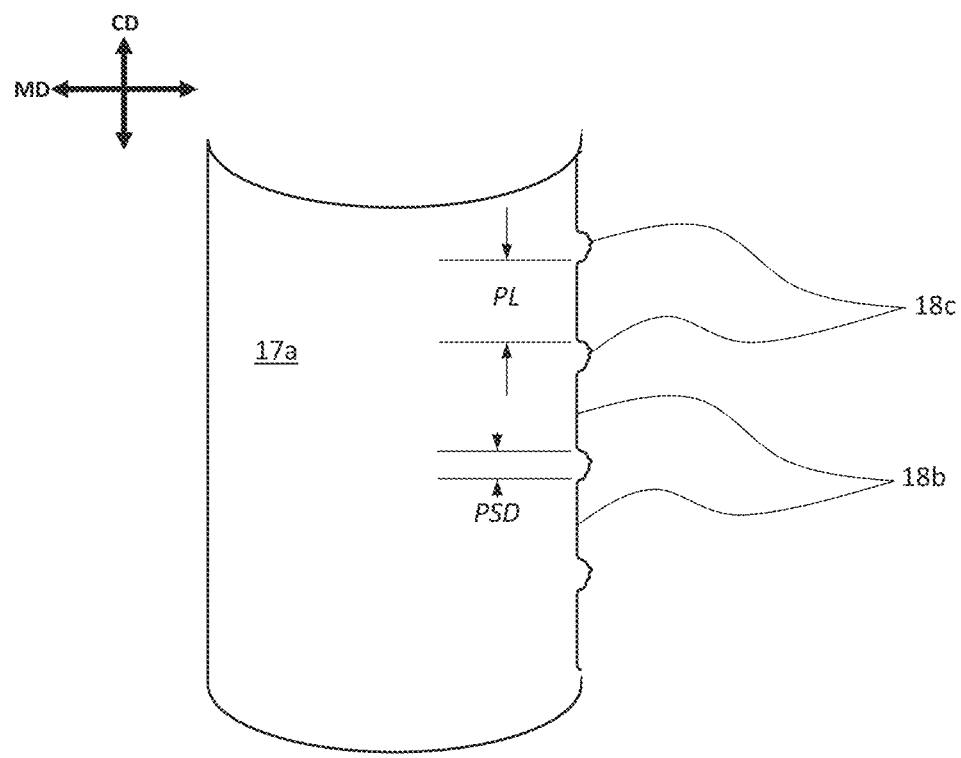
FIG. 13B is an expanded plan view depiction of a portion of the backsheet adhesive coversheet supply web shown in FIG. 13A, following separation along separation perforations to form a backsheet adhesive coversheet.

It will be appreciated that a sufficiently magnified plan view of separated side edges of backsheet adhesive coversheets 17a will approximately reflect such dimensions and ratio. Referring to FIG. 13B, a backsheet adhesive coversheet 17a processed according to the steps described herein (including such perforation step) will have a side edge oriented in the cross direction, having an appearance with features having similarities to those shown in FIG. 13B.

There will be relatively neat edges 18b having cross direction dimensions approximately corresponding to length PL where the perforations were present (relatively easily identifiable and measurable with aid of suitable magnification equipment provided/combined with linear distance measuring aids), and tabs 18c where unperforated portions were present between the perforations, the distal ends of tabs 18c evidencing strain of the uncut portions of the film in the machine direction, to the point of failure of such portions of the film. The separation process imparts the tabs 18c with somewhat irregular lengths and irregularly-shaped distal end edges. Despite these irregularities, however, average lengths PSD and ratios average PL/(average PL+average PSD), or the two in combination, within the ranges set forth above, will result in relatively small and/or closely spaced tabs 18c that are not highly noticeable to the naked eye, retaining a neat appearance for the side edges of the backsheet adhesive coversheet 17a. For purposes herein of determining average values for PL and PSD for a given product, 10 examples of backsheet adhesive coversheets from 10 examples of the product in question are measured, each along a randomly-selected sample portion of the edge in question, 1.6 cm in length. Averages of the 10 measurements for each value are then calculated.

Following separation of the series of pads 10c into individual folded pads in separation unit 307, the individual folded pads may be conveyed to a packaging phasing unit 308, configured to receive the pads and reposition/space them apart along the machine direction by an average predetermined distance suitable for individual packaging described as follows. Suitably spaced, individual folded pads 10a then emerge from packaging phasing unit 308 in configuration (VI) as shown in FIG. 11A.

Figure 14A:
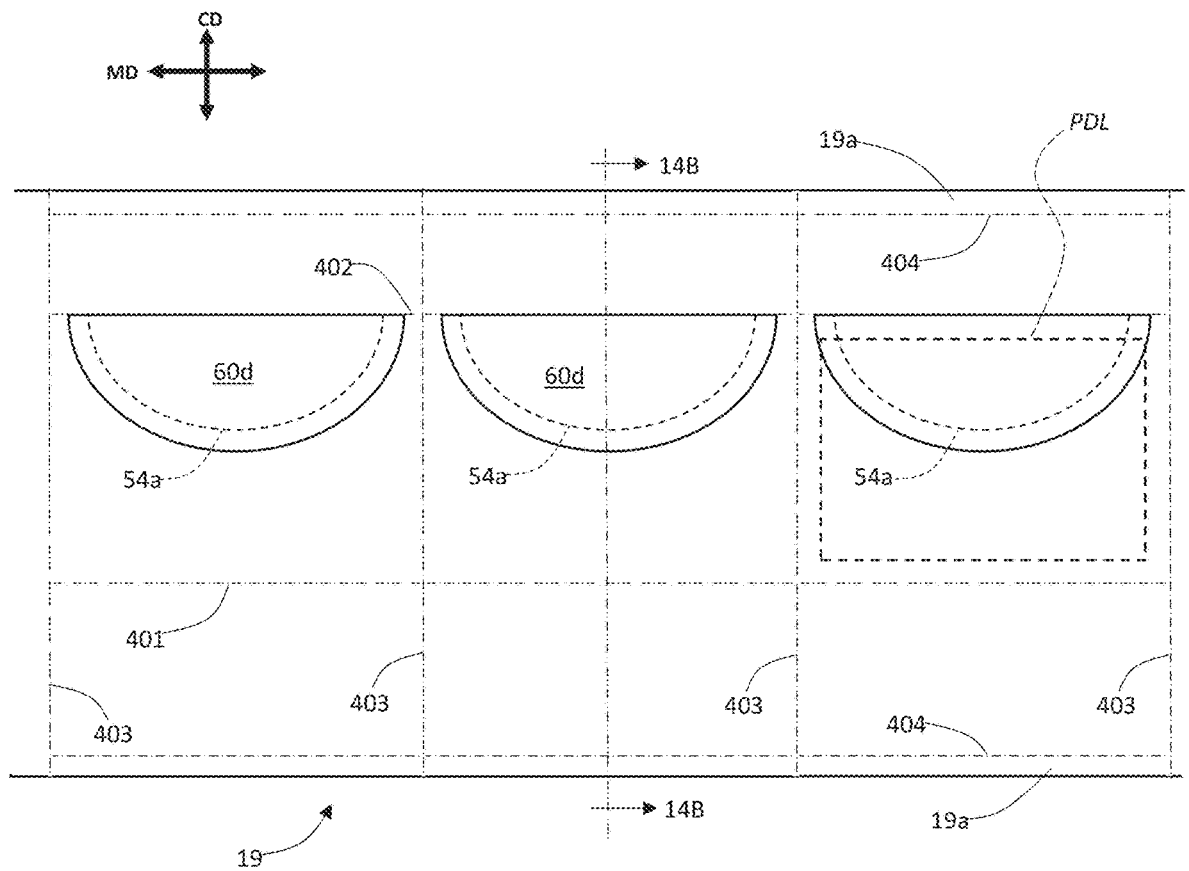
FIG. 14A is a plan view of a portion of continuous package film stock bearing applied flap stickers.
Figure 14B:
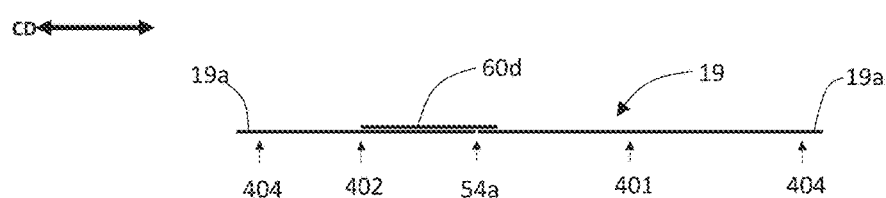
FIG. 14B is a cross section of the package film stock depicted in FIG. 14A, taken along line 14B-14B shown in FIG. 14A.

In configuration (VI), the individual folded, spaced pads 10a may be conveyed to a flow-wrap unit 311. Flow-wrap unit 311 may be configured to receive package film 19 from a package film supply roll 309. In some examples the package film may be predominately polyethylene, of an average caliper no greater than 0.08 mm (80 µm), preferably no greater than 0.065 mm (65 µm) and even more preferably no greater than 0.05 mm (50 µm). Referring to FIGS. 14A and 14B in conjunction with FIG. 11A, package film 19 already bearing pre-applied flap stickers 60d overlying pre-formed package opening cuts or perforations 54a in the film 19, may be received by flow-wrap unit 311. Alternatively, package film 19 may be received already bearing pre-applied flap stickers, but the film may yet to have package opening cuts or perforations 54a provided; and flow-wrap unit 311 may include or be preceded by a package film process unit 310 that provides package opening cuts or perforations 54a in package film 19. Alternatively, package film process unit 310 may be configured to perform either or both of application of flap stickers 60d to the package film 19, and provision of package opening cuts or perforations 54a in the package film 19.

Package opening cuts or perforations 54a may be intermittent perforations or continuous cuts that penetrate substantially or all of the entire thickness/caliper of the package film 19 along the intended path of separation. A supplier of pre-cut package film, or the manufacturer of the product who performs such perforating or cutting, may be provided advantage by application of flap stickers 60d to the film prior to perforating or cutting. Perforating or cutting may be performed continuously using roller-based die-cutting equipment, and the presence of stickers 60d makes it unnecessary to adjust the equipment such that the die cutting blade edges contact an opposing anvil roller to effect a cut through substantially the entire caliper or thickness of the film. Rather, previously-placed flap stickers 60d on the film 19 can effectively provide relatively soft "anvil" surfaces against which the die cutting blades operate. Clearances in the cutting equipment may be adjusted such that the die-cutting blades substantially penetrate/cut through the film 19, but not the flap stickers. In this manner, die cutting blade life may be extended because the die-cutting blade edges are not required to contact a relatively hard surface of an opposing anvil roller.

A continuous cut 54a in the film along the intended opening edge 54, in contrast to intermittent perforations, may provide a benefit for the consumer/user in that no tearing of package film 19 (at uncut or unperforated portions between perforations) is required to open the package, thereby generating less noise by opening the package.

Figure 15:
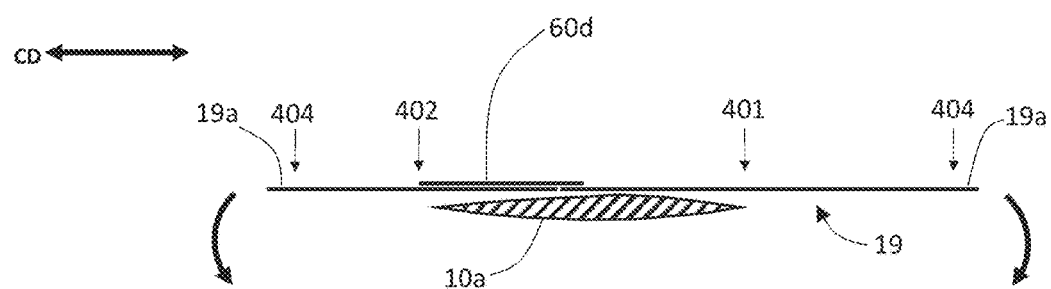
FIG. 15 is a view of the cross section of FIG. 14B, further depicting a location of disposition of a folded pad relative thereto, in preparation for flow wrapping.
Figure 16:
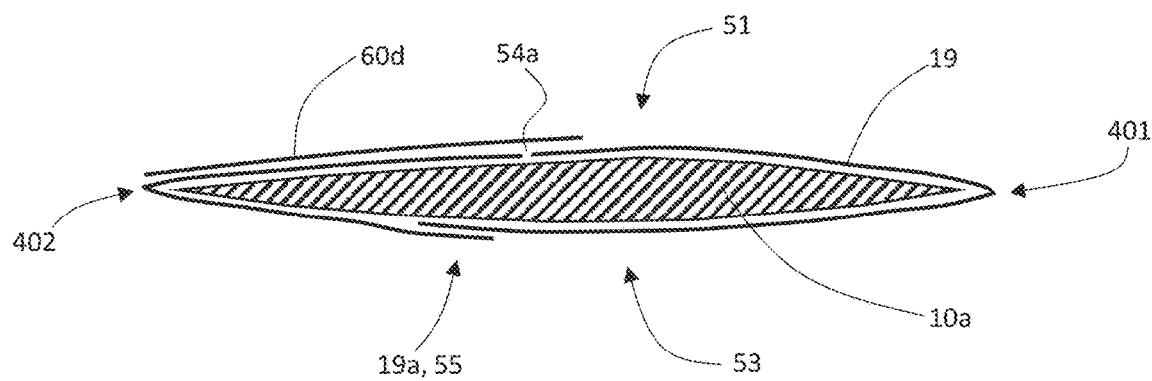
FIG. 16 is an expanded cross section view of the elements depicted in FIG. 15, following their exit from a flow-wrap unit.

As it continuously intakes package film 19, flow-wrap unit 311 also intakes the spaced (phased), individual folded pads 10a and successively disposes them in contact with the film along pre-determined (phased) intervals wherein the pad machine direction spacing corresponds and is registered with the film such that each pad is substantially evenly disposed/aligned between side crimp/seal/cut lines along the cross direction CD of the film, and between package bottom and top fold lines 401 and 402. Such disposition is illustrated by way of example by pad disposition location PDL shown in FIG. 14A. Referring to FIGS. 15 and 16, flow-wrap unit 311 may be configured to then continuously wrap package film 19 over and about the succession of advancing pads 10a (e.g. via plow folding equipment). Referring again to FIG. 14A, package film 19 may be provided with scam margins 19a of extra film material extending (in the cross direction) outboard of seam margin lines 404, to provide material to create a continuous machine-direction seam 55 joining the machine-direction edges of the package film 19 after it is wrapped about the pads 10a. The flow-wrap unit 311 may include or be accompanied by equipment for forming the seams via use of adhesive, via thermal fusion of the package film, or a combination thereof, along the seam margins 19a. The seaming equipment may be configured to form a continuous machine-direction fin scam (such as shown in cross section, by way of example, in FIG. 10B (scam 55)), or alternatively, an overlap scam (such as shown in cross section, by way of example, in FIG. 16 (scam 55)). As previously noted in some examples it may be desired that attachment between the joined sections forming back panel 53, at scam 55, whether effected by adhesive or by welding/fusion of the film, be intermittent or discontinuous and may have spaced intervals of attachment, rather than being continuous, along scam 55. This may be desired to allow venting of air from within the finished package upon compression of the package, such as may occur in processes downstream of package formation, reducing chances that the package will burst open along seams or along the flap closure such as upon compression of the completed package.

A continuous series of flow-wrapped pads 10d emerge from the flow-wrap unit 311 in configuration (VII), also depicted by way of example, in cross section, in FIG. 16. In configuration (VII), the series 10d may be conveyed to a package crimp scaling and cutting unit 312. Package crimp scaling and cutting unit 312 may be configured to continuously receive the series 10d and then, at intervals corresponding to side crimp/seal/cut lines 403 (see FIG. 14) crimp the package film 19 to form front and rear panels 51, 53 together, adhere or fuse the package film of the respective panels to form cross direction side scams 52 (illustrated in, e.g., FIGS. 5A and 9A) and cut the individual packages apart between successive trailing and leading portions of the seamed film material. Individually packaged pads 10e, in configuration (VIII), emerge from the package crimp sealing and cutting unit 312, and may then be conveyed to a stacker (not shown) for controlled collection, orderly stacking and further packaging of quantities of individual packages, as desired. Adhesion or fusion of the package film of the front and rear panels to form side seams 52, and/or cutting between successive leading and trailing packages, may be effected by direct, localized application of heat, ultrasonic energy or any other mechanism suitable to effect localized joining of the film of the front and rear panels. In some examples, seaming and cutting may occur simultaneously, via, e.g., a heated, appropriately shaped knife or die.

In some examples, rather than cutting the individual packages apart entirely as suggested in FIG. 11A, as suggested in FIG. 11B, unit 312 may be configured to create package separation perforations 19a between the formed seams of respective leading and trailing packages, as they pass through the unit, resulting in a continuous chain 10f of individual packages held together by the uncut portions of film within/along the paths of the package separation perforations between the respective package side seams of adjacent leading and trailing packages. This provides a chain of packages 10f that may be gathered by rolling, or folding or festooning with each other in, e.g., accordion-fashion, in a desired quantity, for a desired alternative mode of packaging and/or dispensation. Packages supplied in this mode may be separated from each other by tearing along the package separation perforations 19a.

It is also contemplated that processes by which individual pads are flow-wrapped and envelope packages are formed thereabout, described above, may be applied in other examples wherein the folded pads are conveyed into flow wrapping unit 311 with their longitudinal axes oriented in the machine direction MD, rather than in the cross direction CD as described above. The resulting individually packaged pad will appear in the package with one side edge exposed at the access opening when the package is opening, and the other side edge within the package proximate the opposite, closed end of the package.

Visual Contrast

The color difference measurement is based on the CIE L*a*b* color system (CIELAB). A flatbed scanner capable of scanning a minimum of 24 bit color at 1200 dpi and has manual control of color management (a suitable scanner is an Epson Perfection V750 Pro from Epson America Inc., Long Beach CA) is used to acquire images. The scanner is calibrated against a color reflection target compliant to ANSI method IT8.7/2-1993 using color management software (a suitable package is MonacoEZColor available from X-Rite Grand Rapids, MI) to construct a scanner profile. The resulting calibrated scanner profile is opened within an imaging program that supports sampling in CIE L*a*b* (a suitable program is Photoshop S4 available from Adobe Systems Inc., San Jose, CA) to measure bonded and unbonded areas.

Turn on the scanner for 30 minutes prior to calibration. Place the IT8 target face down onto the scanner glass and close the scanner lid. Open the MonacoEZColor software and select acquire image using the Twain software included with the scanner. Within the Twain software deselect the unsharp mask setting and any automatic color correction or color management options that may be included in the software. If the automatic color management cannot be disabled, the scanner is not appropriate for this application. Acquire a preview scan at 200 dpi and 24 bit color. Insure that the scanned image is straight and first outer surface facing side-up. Crop the image to the edge of the target, excluding all white space around the target, and acquire the final image. The MonacoEZColor software uses this image to compare with included reference files to create and export a calibrated color profile compatible with Photoshop. After the profile is created the scan resolution (dpi) can be changed, but all other settings must be kept constant while imaging samples.

Provide respective samples of each layer 75 mm by 75 mm square. Precondition the samples at about 23° C.±2° C. and about 50%±2% relative humidity for 2 hours prior to testing.

Open the scanner lid and place the first sample onto the scanner glass with the first outer surface facing the glass. Cover the sample with the white background (in this test method white is defined as having L*>94, −2<a*<2, and −2<b*<2) and close the lid. Acquire and import a scan of the first sample into Photoshop at 600 dpi and 24 bit color. Assign the calibrated scanner profile to the image and change the mode to Lab Color ("Lab Color" in Photoshop corresponds to the CIE L*a*b*standard). Select the "eyedropper" color selection tool. Set the sampling size of the tool to include as many pixels as possible within an area of the sample 2 mm by 2 mm square. Using the eyedropper tool measure and record L*a*b* values in 10 different 2 mm by 2 mm square areas (not having apertures) in the sample image. Average the 10 individual L*a*b* values and record as L1, a1, and b1 respectively.

Repeat the steps in the paragraph above for the second sample, and record the averaged values as L2, a2 and b2. Calculate and report the color difference (delta E*) between the bonded and unbonded areas using the following equation:

$$\text{delta } E^* = \sqrt{(L_2^* - L_1^*)^2 + (a_2^* - a_1^*)^2 + (b_2^* - b_1^*)^2}$$

and report to the nearest 0.01 units. A total of three substantially identical samples of each layer are measured for each sample set. Average the three delta E* values and report to the nearest 0.1 unit.

In view of the foregoing description, the following non-limiting examples are contemplated:

1. A product comprising a feminine hygiene pad (10) provided in a folded configuration within an individualized package, the pad comprising a liquid permeable topsheet (20), a liquid impermeable backsheet (30), and an absorbent layer (40) comprising a continuous section of resilient polymeric open-celled foam material disposed between the topsheet and the backsheet, the pad having an unfolded and flattened length along a longitudinal axis no greater than 32 cm;

wherein the pad is provided in a folded configuration wherein the pad is folded over on itself along at least three lateral fold lines (201, 202, 203) defining at least three folds, which divide the length into at least first, second, third and fourth sublengths of the pad (210, 211, 212, 213) which in the folded configuration all overlie or underlie each other directly or indirectly, the first sublength being proximate a forward end (12) of the pad, the second sublength being adjacent the first sublength, the third sublength being adjacent the second sublength, and the fourth sublength being adjacent the third sublength at a forward portion of the fourth sublength, and proximate a rearward end (14) of the pad at a rearward portion of the fourth sublength;

wherein the topsheet lies to the inside of each of the three folds and the backsheet lies to the outside of each of the three folds;

wherein the pad in the folded configuration has a singularized main fold nose (214);

wherein the pad in the folded configuration is folded separately of the package and is contained within the package, and wherein the package comprises a section of polymeric film and is configured to provide an access opening exposing the pad.

2. The product of example 1 wherein the wherein the pad has total absorption capacity, and the polymeric foam material provides at least half, more preferably at least 75 percent, and still more preferably at least 90 percent of the total absorption capacity, wherein absorption capacity of the pad and of the polymeric foam material of the absorbent layer separate from the pad are both measured by any single method known in the art.

3. The product of either of examples 1 or 2 wherein the polymeric foam material is a HIPE foam material.

4. The product of any of examples 1-3 wherein the section of polymeric foam material comprises first and second sublayers (40a, 40b) in contact, wherein the first sublayer has a first average cell size and the second sublayer has a second average cell size, and the first average cell size is greater than the second average cell size.

5. The product of example 4 wherein the first sublayer is disposed between the topsheet and the second sublayer, and the second sublayer is disposed between the first sublayer and the backsheet.

6. The product of any of the preceding examples wherein the package comprises an envelope structure (50) having two oppositely-disposed longitudinal side edges, an opening edge (54) and a flap edge (59), the film being folded into the envelope structure comprising two envelope side edges corresponding to the longitudinal side edges, a first lateral fold forming the film into a pocket structure in which the access opening is formed in part by the opening edge, and a second lateral fold forming a flap of the film extending from a second lateral fold line (56), the flap being sized and configured to overlie the opening edge and close the envelope about the pad, the film being joined to itself to form seams (52) along the respective longitudinal side edges and envelope side edges to close respective sides of the envelope structure, the envelope structure also being provided with a closure element to releasably hold the flap in a closed position and retain the pad within the envelope.

7. The product of any of the preceding examples wherein the pad is oriented within the package such that the singularized main fold nose (214) is proximate the access opening.

8. The product of any of the preceding examples wherein the section of polymeric foam material is disposed directly beneath the topsheet.

9. The product of any of the preceding examples wherein the polymeric film comprises polyethylene.

10. The product of any of the preceding examples wherein the polymeric film has an inner surface and an outer surface corresponding to respective inner and outer surfaces of the package, the inner surface has a first visible color or design attribute, the pad has an outer pad surface visible immediately after the package is first opened, the outer pad surface having a second visible color or design attribute, and the second visible color or design attribute is visually distinguishable from the first visible color or design attribute.

11. The product of example 10 wherein the inner surface as compared with the outer pad surface exhibits a delta E* of at least 2.0, more preferably at least 3.5.

12. The product of any of the preceding examples having an uncompressed caliper when laid flat on a horizontal surface, no greater than 25 mm and more preferably no greater than 20 mm.

13. The product of any of the preceding examples wherein the backsheet and topsheet are separate and discrete from the polymeric film.

14. The product of example 13 wherein the pad has no substantial attachment to the film comprised by the package.

15. The product of any of the preceding examples wherein the folded configuration is a roll fold configuration.

16. The product of any of examples 1-14 wherein the folded configuration is a book jacket fold configuration.

17. The product of any of the preceding examples wherein the section of polymeric foam material has a pattern of perforations therein.

18. The product of any of the preceding examples wherein the pad in the folded configuration does not comprise any longitudinal folds that traverse the section of polymeric foam material.

19. A product comprising a feminine hygiene pad (10) provided in a folded configuration within an individualized package (50), the pad comprising a liquid permeable topsheet (20), a liquid impermeable backsheet (30), and an absorbent layer (40) disposed between the topsheet and the backsheet;

wherein the pad is provided in a folded configuration wherein the pad is folded over on itself along at least two lateral fold lines (201, 202) defining at least two folds, which divide the length into at least first, second and third sublengths of the pad (210, 211, 212) which in the folded configuration all overlie or underlie each other directly or indirectly, the first sublength being proximate a forward end (12) of the pad, the second sublength being adjacent the first sublength, the third sublength being adjacent the second sublength at a forward portion of the third sublength, and proximate a rearward end (14) of the pad at a rearward portion of the third sublength;

wherein the topsheet lies to the inside of each of the three folds and the backsheet lies to the outside of each of the three folds;

wherein the pad in the folded configuration has a singularized main fold nose (214);

wherein the pad in the folded configuration is folded separately of the package and is contained within the package, wherein the package comprises a section of polymeric film and is configured to provide an access opening exposing the pad;

wherein the pad in the folded configuration is disposed within the package with the singularized main fold nose proximate the access opening.

20. The product of example 19 wherein the pad has an unfolded and flattened length along a longitudinal axis no greater than 32 cm.

21. The product of either of examples 19 or 20 wherein the pad is folded over on itself along at least three lateral fold lines (201, 202, 203) defining at least three folds, which divide the length into first, second, third and fourth sublengths of the pad which in the folded configuration all overlie or underlie each other directly or indirectly, the first sublength being proximate a forward end of the pad, the second sublength being adjacent the first sublength, the third sublength being adjacent the second sublength, and the fourth sublength being adjacent the third sublength at a forward portion of the fourth sublength, and proximate a rearward end of the pad at a rearward portion of the fourth sublength.

22. The product of either of examples 19-21 wherein the package (50) comprises an envelope structure having two oppositely-disposed longitudinal side edges, an opening end edge (54) and a flap end edge (59), the film being folded into the envelope structure comprising two envelope side edges corresponding to the longitudinal side edges, a first lateral fold forming the film into a pocket structure in which the access opening is formed in part by the opening edge, and a second lateral fold forming a flap of the film extending from the second lateral fold and sized and configured to overlie the opening edge and close the envelope about the pad, the film being joined to itself along the respective longitudinal side edges and envelope side edges to close respective sides of the envelope structure and form side seams (52), the envelope structure also being provided with a closure element (60a, 60b, 60c, 60e) to releasably hold the flap in a closed position and retain the pad within the envelope.

23. The product of any of examples 19-22 wherein the polymeric film comprises polyethylene.

24. The product of any of examples 19-23 wherein the polymeric film has outer and inner surfaces corresponding to outer and inner surfaces of the envelope, the inner surface has a first visible color or design attribute, the pad in its folded configuration has a second visible color or design attribute, and the second visible color or design attribute is visually distinguishable from the first visible color or design attribute.

25. The product of any of examples 19-24 having an uncompressed caliper when laid flat on a horizontal surface, no greater than 25 mm and more preferably no greater than 20 mm.

26. The product of any of examples 19-25 wherein the backsheet and topsheet are separate and discrete from the polymeric film.

27. The product of any of examples 19-26 wherein the pad has no substantial attachment to the film comprised by the package.

28. The product of any of examples 19-27 wherein the folded configuration is a roll fold configuration.

29. The product of any of examples 19-27 wherein the folded configuration is a book jacket fold configuration.

30. The product of any of the preceding examples wherein the access opening is defined in part by an edge (54) of a package panel that is partially cut away to expose a portion of the folded pad in addition to the singularized main fold nose.

31. A product comprising a feminine hygiene pad (10) having a pad length ($L_P$) and provided in a folded configuration within an individualized package (50), the pad comprising a liquid permeable topsheet (20), a liquid impermeable backsheet (30), and an absorbent layer (40) disposed between the topsheet and the backsheet;

wherein the pad is provided in a folded configuration wherein the pad is folded over on itself along at least one lateral fold line (201, 202, 203) defining a corresponding number of folds, which divide(s) the length into a plurality of sublengths of the pad which in the folded configuration overlie or underlie each other directly or indirectly, wherein the pad in the folded configuration is folded separately of the package and is contained within the package, wherein the package comprises a section of polymeric film and is configured to provide an access opening exposing the pad; and wherein the pad comprises a backsheet adhesive coversheet (17a) comprising a section of polymeric coversheet film adhered to an outward-facing side of the backsheet, and a deposit of backsheet adhesive (35) disposed between the backsheet adhesive coversheet and the backsheet, the backsheet, the backsheet adhesive coversheet and the backsheet adhesive being selected and adapted such that the backsheet adhesive coversheet may be peeled away from the pad to expose the backsheet adhesive without substantial damage to a remainder of the pad, and such that the backsheet adhesive remains substantially in place and adhered to the backsheet following peeling away of the backsheet adhesive coversheet.

32. The product of example 31 wherein the pad in the folded configuration has a singularized main fold nose (214) and the pad in the folded configuration is disposed within the package with the singularized main fold nose proximate the access opening.

33. The product of either of examples 31 or 32 wherein the backsheet adhesive coversheet (17a) has a backsheet adhesive coversheet length that is less than the pad length.

34. The product of any of examples 31-33 wherein the backsheet adhesive coversheet has longitudinally-oriented side edges that exhibit features of separation of the backsheet adhesive coversheet from leading and trailing backsheet adhesive coversheets of respective leading and trailing pads during manufacture on a continuous manufacturing line, via separation under tension of backsheet adhesive coversheet stock material comprised by the respective backsheet adhesive coversheets, along lines of separation (18) of the backsheet adhesive coversheet stock material (17) proximate the side edges of the respective leading and trailing pads.

35. The product of example 34 wherein the features of separation reflect perforations (18a) that were present in the backsheet adhesive coversheet stock material along the lines of separation.

36. The product of example 35 wherein the features of separation reflect perforations having an average length PL of 0.4 mm to 3.5 mm; more preferably 0.45 mm to 2.0 mm; and even more preferably 0.5 mm to 1.0 mm.

37 The product of either of examples 35 or 36 wherein the features of separation reflect perforations having a ratio average PL/(average PL+average PSD) of 0.15 to 0.70; more preferably 0.25 to 0.55; and even more preferably 0.30 to 0.50.

38. The product of any examples 31-37 wherein the package comprises an envelope structure (50) comprising the section of polymeric film and having two oppositely-disposed longitudinal side edges with longitudinal side seams (52) therealong, a folded bottom edge, and an opening flap (58) extending from a proximal portion along a folded top edge to a distal edge (59), and configured to be openable to provide the access opening.

39. The product of example 38 wherein the package comprises an overlap seam (55) extending in a lateral direction from one of the seamed side edges to the other of the seamed side edges.

40. The product of example 39 wherein the overlap seam (55) comprises a joining of two sections of polymeric film via a seam adhesive.

41. The product of any of examples 37-40 comprising a discrete flap sticker (60) adhered to and overlying the opening flap (58).

42. The product of example 41 wherein a portion of polymeric film underlying the flap sticker has been substantially continuously scored or cut through its thickness so as to cause or facilitate separation of the portion of polymeric film from itself to define the flap, upon lifting of the flap closure sticker, without the need to tear the polymeric film.

43. The product of any of examples 38-42 wherein the side seams (52) comprise portions of a front-facing portion of the polymeric film and a rear-facing portion of the polymeric film that are attached along the respective side edges via fusing.

44. The product of example 43 wherein the thermally fused portions of the polymeric film along each of the side edges have an average width no greater than 6 mm, more preferably no greater than 4 mm, and still more preferably no greater than 3 mm.

45. A method for manufacturing feminine hygiene pad products, comprising the steps of:
    providing a continuous stream of feminine hygiene pads (10) moving along a machine direction MD on a conveyor, each of the pads comprising a longitudinal axis (100) and a topsheet (20), a backsheet (30), an outward-facing surface, and an absorbent structure (40) disposed between the topsheet and the backsheet;
    orienting each of the pads in the stream such that its longitudinal axis is substantially aligned with a cross direction CD perpendicular to the machine direction;
    providing a supply of a continuous web of backsheet adhesive coversheet material (17) moving along the machine direction,
        wherein the backsheet coversheet material bears a series of previously provided spaced separation perforations (18) along lines of separation aligned in the cross direction, or
        a series of spaced separation perforations (18) along lines of separation aligned in the cross direction are provided following provision of the continuous web of backsheet adhesive coversheet material;
    providing deposits of backsheet adhesive between the continuous web of backsheet adhesive coversheet material and outward-facing surfaces of the pads;
    successively disposing the outward-facing surfaces of the oriented pads in the stream, in contact with the continuous web of backsheet adhesive coversheet material, each pad being disposed substantially between respective leading and following separation perforations (18) on the continuous web of backsheet adhesive coversheet material, wherein the pads are adhered to the continuous web of backsheet adhesive coversheet material by the deposits of backsheet adhesive; and
    following such disposition of pads in contact with the continuous web of backsheet material, successively separating each pad, together with a portion of the continuous web of backsheet material from a following pad, and from the continuous web of backsheet material, along the separation perforations, thereby creating individual pads (10*a*) each bearing an individual backsheet adhesive coversheet (17*a*).

46. The method of example 45 further comprising the step of folding the oriented pads along one or more lateral fold lines (201, 202, 203) following their disposition in contact with the continuous web of backsheet adhesive coversheet material, and prior to the successive separation of each pad from a following pad.

47. The method of either of examples 45 or 46 further comprising the step of conveying the separated pads successively into a flow wrap machine (311), and flow wrapping the pads in a package film (19).

48. The method of any of examples 45-47 wherein the continuous web of backsheet adhesive coversheet material (17) has a cross direction dimension that is less than an average length ($L_P$) of the pads.

49. The method of any of examples 45-48 wherein the spaced separation perforations (18) are spaced along the machine direction by an average spacing PS that is no greater than 125 percent of an average width of the pads, more preferably no greater than 120 percent of the average width of the pads, and even more preferably no greater than 115 percent of the average width of the pads.

50. A product comprising a feminine hygiene pad (10) in a folded configuration provided within an individualized envelope package (50) having a front panel (51) and a rear panel (53);
    wherein the pad in the folded configuration is folded separately of the envelope package and is entirely contained within the package,
    wherein the envelope package has a rectangular shape and comprises:
        a section of polymeric film (19);
        a pair of oppositely-disposed, substantially straight and substantially parallel side seams (52) along which respective portions of the polymer film forming the front panel (51) and rear panel (53) are attached to each other, the seams having a length;
        a top edge extending from one side seam to the other when the package is in a closed configuration;
        a closure flap (58), having a proximal portion proximate the top edge, and terminating at a distal edge (59), wherein:
            the package is configured to create an access opening upon lifting of the closure flap at the distal edge, the access opening having an opening edge (54),
            the closure flap (58) overlaps the opening edge (54); and
            the closure flap may be lifted to create the access opening while allowing material along the side seams to remain unseparated along a majority, substantially all, or all of respective lengths of the side seams.

51. The product of example 50 wherein the closure flap comprises a flap sticker (60*d*) that overlaps and covers the opening edge (54).

52. The product of example 51 wherein the opening edge (54) has a path length, and the flap sticker (60*d*) overlaps and covers the opening edge over a majority of the path length, preferably the entirety of the path length.

53. The product of any of examples 50-52 wherein the opening edge (54) is formed by perforating or cutting a portion of the polymeric film forming a front panel (51) of the envelope package, along a path of separation.

54. The product of either of examples 51 or 52 wherein the opening edge (54) is formed by perforating or cutting a portion of the polymeric film forming a front panel (51) of the envelope package along a path of separation defining the opening edge, and the overlapping flap sticker (60*d*) with adhesive (60*e*) thereon holds the flap in a closed position.

55. The product of any of examples 50-54 wherein the opening edge (54) is oriented transversely to the side seams.

56. The product of any of examples 50-55 wherein the opening edge (54) follows a curving path.

57. The product of example 56 wherein the pad in the folded configuration has a first dimension measured parallel to the side seams and a second dimension measured perpendicular to the side seams, and when the package is in an opened configuration, the curving path exposes a greatest portion of the first dimension at a location between the side seams (52).

58. The product of any of examples 50-57 wherein the pad in the folded configuration has a singularized main fold nose 214, and the pad is oriented within the envelope package such that the singularized main fold nose is exposed by the access opening.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed:

1. A product comprising a feminine hygiene pad having a pad length $L_P$ and provided in a folded configuration within an individualized package, the pad comprising a liquid permeable topsheet, a liquid impermeable backsheet, and an absorbent layer disposed between the topsheet and the backsheet;
   wherein the pad is provided in a folded configuration, wherein the pad is folded over on itself along at least one lateral fold line defining a corresponding number of folds dividing the pad length into a plurality of sublengths, wherein the sublengths in the folded configuration overlie or underlie each other directly or indirectly,
   wherein the pad in the folded configuration is folded separately of the package and is contained within the package,
   wherein the package comprises an access opening configured to expose the pad; and
   wherein the pad comprises a coversheet joined to an outward-facing side of the backsheet, and a deposit of backsheet adhesive disposed between the coversheet and the backsheet, wherein the coversheet comprises a longitudinally-oriented side edge comprising two or more tabs and one or more neat edges, wherein the one or more neat edges has an average length PL of from about 0.4 mm to about 3.5 mm, wherein the backsheet, the coversheet, and the backsheet adhesive being selected and adapted such that the coversheet may be peeled away from the pad to expose the backsheet adhesive without substantial damage to a remainder of the pad, and such that the backsheet adhesive remains substantially in place and adhered to the backsheet following peeling away of the coversheet.

2. The product of claim 1, wherein the pad in the folded configuration has a singularized main fold nose and the pad in the folded configuration is disposed within the package with the singularized main fold nose proximate the access opening.

3. The product of claim 1, wherein the coversheet has a coversheet length that is less than the pad length.

4. The product of claim 1, wherein the coversheet comprises two longitudinally-oriented side edges that comprise a plurality of neat edges and a plurality of tabs from separation of the coversheet from leading and trailing coversheets of respective leading and trailing pads during manufacture on a continuous manufacturing line, via separation under tension of coversheet stock material comprised by the respective coversheets, along lines of separation of the coversheet stock material proximate the side edges of the respective leading and trailing pads.

5. The product of claim 1, wherein the one or more neat edges reflect perforations that were present in the coversheet stock material along the lines of separation.

6. The product of claim 5, wherein the one or more neat edges having an average length PL of 0.5 mm to 1.0 mm.

7. The product of claim 5, wherein the one or more neat edges having a ratio average PL/(average PL+average PSD) of 0.30 to 0.50.

8. The product of claim 1, wherein the package comprises an envelope structure comprising the section of material and having two oppositely-disposed longitudinal side edges with longitudinal side seams therealong, a folded bottom edge, and an opening flap extending from a proximal portion along a folded top edge to a distal edge, and configured to be openable to provide the access opening.

9. The product of claim 8, wherein the package comprises an overlap seam extending in a lateral direction from one of the seamed side edges to the other of the seamed side edges.

10. The product of claim 9, wherein the overlap seam comprises a joining of two sections of material.

11. The product of claim 1, wherein the package comprises a section of a polymeric film, a nonwoven web material, or a laminate of at least one of the polymeric film and the nonwoven web material.

12. The product of claim 11, comprising a discrete flap sticker adhered to and overlying an opening flap.

13. The product of claim 12, wherein a portion of the section of the package underlying the flap sticker has been substantially continuously scored or cut through its thickness so as to cause or facilitate separation of the portion of the package from itself to define the flap, upon lifting of the flap closure sticker.

14. The product of claim 8, wherein the side seams comprise portions of a front-facing portion of the polymeric film and a rear-facing portion of the polymeric film that are attached along the respective side edges via fusing to form thermally fused portions.

15. The product of claim 14, wherein the thermally fused portions of the polymeric film along each of the side edges have an average width no greater than 4 mm.

16. A product comprising a feminine hygiene pad having a pad length $L_P$ and provided in a folded configuration within an individualized package, the pad comprising a liquid permeable topsheet, a liquid impermeable backsheet, and an absorbent layer disposed between the topsheet and the backsheet;

wherein the pad is provided in a roll fold configuration or a book jacket fold configuration wherein the pad is folded over on itself along at least one lateral fold line defining a corresponding number of folds dividing the length into a plurality of sublengths of the pad, wherein the sublengths in the folded configuration overlie or underlie each other directly or indirectly, wherein the pad in the folded configuration is folded separately of the package and is contained within the package, wherein the package is configured to provide an access opening exposing the pad; and wherein the pad comprises a coversheet joined to an outward-facing side of the backsheet, and a deposit of backsheet adhesive disposed between the coversheet and the backsheet, wherein the backsheet, the coversheet and the backsheet adhesive being selected and adapted such that the coversheet may be peeled away from the pad to expose the backsheet adhesive without substantial damage to a remainder of the pad, wherein the coversheet comprises a longitudinally-oriented side edge comprising two or more tabs and one or more neat edges, wherein the one or more neat edges has an average length PL of from about 0.4 mm to about 3.5 mm, and wherein the one or more neat edges having a ratio average PL/(average PL+average PSD) of 0.15 to 0.70.

17. The product of claim 16, wherein the coversheet has a width and the pad has an average width, and wherein the width of the coversheet is greater than 100 percent and no greater than 125 percent of the average width of the pad.

18. The product of claim 16, wherein the package comprises at least one of a polymeric film and a nonwoven web material.

19. The product of claim 16, wherein the package comprises a laminate of at least one of a polymeric film and a nonwoven web material.

20. The product of claim 16, wherein the coversheet has a coversheet length that is less than the pad length.

* * * * *